Figure 1:
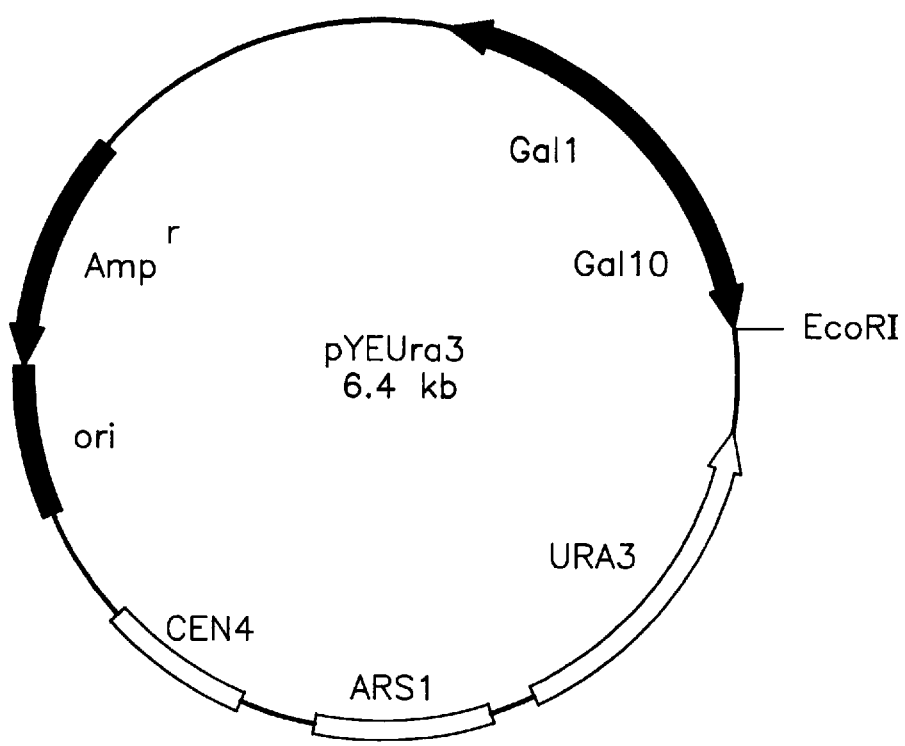

United States Patent [19]
Revuelta Doval et al.

[11] Patent Number: 5,821,090
[45] Date of Patent: Oct. 13, 1998

[54] RIBOFLAVIN-BIOSYNTHESIS IN FUNGI

[75] Inventors: Jose Luis Revuelta Doval; Maria Jose Buitrago Serna, both of Salamanca; Maria Angeles Santos Garcia, Santa Maria, all of Spain

[73] Assignee: BASF Aktiengesellschaft, Ludwigsshafen, Germany

[21] Appl. No.: 716,301

[22] PCT Filed: Mar. 15, 1995

[86] PCT No.: PCT/EP95/00958

§ 371 Date: Sep. 24, 1996

§ 102(e) Date: Sep. 24, 1996

[87] PCT Pub. No.: WO95/26406

PCT Pub. Date: Oct. 5, 1995

[30] Foreign Application Priority Data

Mar. 25, 1994 [DE] Germany ............... 44 10 382.4
Jun. 15, 1994 [DE] Germany ............... 44 20 785.9

[51] Int. Cl.$^6$ ............... C07H 21/04; C12N 15/00; C12N 1/14; C12P 19/40
[52] U.S. Cl. ............... 435/88; 435/66; 435/254.1; 435/254.11; 435/254.2; 435/254.21; 435/254.22; 435/320.1; 435/325; 536/23.2; 935/22
[58] Field of Search ............... 435/66, 254.1, 435/254.11, 254.2, 254.21, 254.22, 320.1, 88, 325; 536/23.2; 935/22

[56] References Cited

PUBLICATIONS

Ngo et al. (1994) Computational Complexity, Protein Stucture Prediction, and the Levinthal Paradox. In: The Protein Folding Problem and Tertiary Structure Prediction. Eds. Merz et al., Birkhauser, Boston, MA, pp. 491–495, Jan. 1994.

Buitrago et al., *Yeast*, vol. 9, No. 10, Oct. 1993, pp. 1099–1102.

Diognon et al., *Yeast*, vol. 9, No. 2, 1993, pp. 189–199.

*The Merck Index*, pp. 1183 and 1983.

Watson et al., *Molcular Biology of the Gene*, 4$^{th}$ Ed., vol. 1, 1987, pp. 86–87 and 437–440.

Moore et al., *Nature Biotech.*, vol. 14, 1996, pp. 458–467).

SPEE et al., *Nucleic Acids Research*, 1993, vol. 21, No. 3, 1993, pp. 777–778.

Rellos et al., *Prot. Expres. and Purif.*, vol. 5, 1994, pp. 270–277.

Mehta et al., *Indian Journal of Experimental Biology*, vol. 18, Mar. 1980, pp. 243–244.

Hollander et al., *Biochem. and Biophys. Res. Comm.*, vol. 89, 1979, pp. 759–763.

Richter et al., *J. og Bacteriology*, vol. 174, 1992, pp. 4050–4056.

Winestock et al., *J. of Biol. Chem.*, vol. 238, No. 8, Aug. 1963, pp. 2866–2874.

*Primary Examiner*—Robert A. Wax
*Assistant Examiner*—Einar Stole
*Attorney, Agent, or Firm*—Keil & Weinkauf

[57] ABSTRACT

The present invention relates to the genes for riboflavin biosynthesis in the fungus Ashbya gossypii and to genetic engineering processes for preparing riboflavin using these genes and gene products.

9 Claims, 7 Drawing Sheets

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 1329 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Ashbya gossypii ( i x ) FEATURE:
        ( A ) NAME/KEY: 5'UTR
        ( B ) LOCATION: 1..242

( i x ) FEATURE:
        ( A ) NAME/KEY: CDS
        ( B ) LOCATION: 243..1148

( i x ) FEATURE:
        ( A ) NAME/KEY: 3'UTR
        ( B ) LOCATION: 1149..1329

( x i ) SEQUENCE DESCRIPTION: SEQ ID NO: 1:

```
TTTCTGTCCG  CATACTTCAT  ATGCTCATCG  CACATTGATA  ATGTACATTC  GAAAAATTTC         60

AAGATTAGCC  TCCGTGAACA  GCGATTTACC  TTAGGCAAAA  GTAACAAAAG  GCTTTTCCGT        120

AGGTGCTTTG  TCATTCAACA  ATCCACGTCG  GAATTGGCGA  CTATATAGTG  TAGGGCCCAT        180

AAAGCAGTAG  TCGGTGTTGA  TAGCTGTGTC  AGACCAACTC  TTTGTTAATT  ACTGAAGCTG        240
```

```
AT  ATG  ACT  GAA  TAC  ACA  GTG  CCA  GAA  GTG  AGG  TGT  GTC  GCA  CGC  GCG        287
    Met  Thr  Glu  Tyr  Thr  Val  Pro  Glu  Val  Arg  Cys  Val  Ala  Arg  Ala
     1              5                   10                  15

CGC  ATA  CCG  ACG  GTA  CAG  GGC  ACC  GAT  GTC  TTC  CTC  CAT  CTA  TAC  CAC         335
Arg  Ile  Pro  Thr  Val  Gln  Gly  Thr  Asp  Val  Phe  Leu  His  Leu  Tyr  His
                      20                  25                      30

AAC  TCG  ATC  GAC  AGC  AAG  GAA  CAC  CTA  GCG  ATT  GTC  TTC  GGC  GAG  AAC         383
Asn  Ser  Ile  Asp  Ser  Lys  Glu  His  Leu  Ala  Ile  Val  Phe  Gly  Glu  Asn
              35                      40                      45

ATA  CGC  TCG  CGG  AGT  CTG  TTC  CGG  TAC  CGG  AAA  GAC  GAC  ACG  CAG  CAG         431
Ile  Arg  Ser  Arg  Ser  Leu  Phe  Arg  Tyr  Arg  Lys  Asp  Asp  Thr  Gln  Gln
                 50                     55                  60

GCG  CGG  ATG  GTG  CGG  GGC  GCC  TAC  GTG  GGC  CAG  CTG  TAC  CCC  GGG  CGG         479
Ala  Arg  Met  Val  Arg  Gly  Ala  Tyr  Val  Gly  Gln  Leu  Tyr  Pro  Gly  Arg
         65                      70                      75

ACC  GAG  GCA  GAC  GCG  GAT  CGG  CGT  CAG  GGC  CTG  GAG  CTG  CGG  TTT  GAT         527
Thr  Glu  Ala  Asp  Ala  Asp  Arg  Arg  Gln  Gly  Leu  Glu  Leu  Arg  Phe  Asp
 80                      85                      90                      95

GAG  ACA  GGG  CAG  CTG  GTG  GTG  GAG  CGG  GCG  ACG  ACG  TGG  ACC  AGG  GAG         575
Glu  Thr  Gly  Gln  Leu  Val  Val  Glu  Arg  Ala  Thr  Thr  Trp  Thr  Arg  Glu
                        100                     105                     110

CCG  ACA  CTG  GTG  CGG  CTG  CAC  TCG  GAG  TGT  TAC  ACG  GGC  GAG  ACG  GCG         623
Pro  Thr  Leu  Val  Arg  Leu  His  Ser  Glu  Cys  Tyr  Thr  Gly  Glu  Thr  Ala
                    115                     120                     125

TGG  AGC  GCG  CGG  TGC  GAC  TGC  GGG  GAG  CAG  TTC  GAC  CAG  GCG  GGT  AAG         671
```

|     |     |     |     |     |     |     |     |     |     |     |     |     |     |     |     |
|---|---|---|---|---|---|---|---|---|---|---|---|---|---|---|---|
| Trp | Ser | Ala | Arg | Cys | Asp | Cys | Gly | Glu | Gln | Phe | Asp | Gln | Ala | Gly | Lys |
|     |     | 130 |     |     |     |     | 135 |     |     |     |     | 140 |     |     |     |

```
CTG  ATG  GCT  GCG  GCG  ACA  GAG  GGC  GAG  GTG  GTT  GGC  GGT  GCG  GGG  CAC    719
Leu  Met  Ala  Ala  Ala  Thr  Glu  Gly  Glu  Val  Val  Gly  Gly  Ala  Gly  His
     145                      150                     155

GGC  GTG  ATC  GTG  TAC  CTG  CGG  CAG  GAG  GGC  CGC  GGC  ATC  GGG  CTA  GGC    767
Gly  Val  Ile  Val  Tyr  Leu  Arg  Gln  Glu  Gly  Arg  Gly  Ile  Gly  Leu  Gly
160                      165                     170                      175

GAG  AAG  CTG  AAG  GCG  TAC  AAC  CTG  CAG  GAC  CTG  GGC  GCG  GAC  ACG  GTG    815
Glu  Lys  Leu  Lys  Ala  Tyr  Asn  Leu  Gln  Asp  Leu  Gly  Ala  Asp  Thr  Val
                    180                      185                     190

CAG  GCG  AAC  GAG  CTG  CTC  AAC  CAC  CCT  GCG  GAC  GCG  CGC  GAC  TTC  TCG    863
Gln  Ala  Asn  Glu  Leu  Leu  Asn  His  Pro  Ala  Asp  Ala  Arg  Asp  Phe  Ser
               195                      200                     205

TTG  GGG  CGC  GCA  ATC  CTA  CTG  GAC  CTC  GGT  ATC  GAG  GAC  ATC  CGG  TTG    911
Leu  Gly  Arg  Ala  Ile  Leu  Leu  Asp  Leu  Gly  Ile  Glu  Asp  Ile  Arg  Leu
          210                      215                     220

CTC  ACG  AAT  AAC  CCC  GAC  AAG  GTG  CAG  CAG  GTG  CAC  TGT  CCG  CCG  GCG    959
Leu  Thr  Asn  Asn  Pro  Asp  Lys  Val  Gln  Gln  Val  His  Cys  Pro  Pro  Ala
     225                      230                     235

CTA  CGC  TGC  ATC  GAG  CGG  GTG  CCC  ATG  GTG  CCG  CTT  TCA  TGG  ACT  CAG   1007
Leu  Arg  Cys  Ile  Glu  Arg  Val  Pro  Met  Val  Pro  Leu  Ser  Trp  Thr  Gln
240                      245                     250                      255

CCC  ACA  CAG  GGC  GTG  CGC  TCG  CGC  GAG  CTG  GAC  GGC  TAC  CTG  CGC  GCC   1055
Pro  Thr  Gln  Gly  Val  Arg  Ser  Arg  Glu  Leu  Asp  Gly  Tyr  Leu  Arg  Ala
                    260                      265                     270

AAG  GTC  GAG  CGC  ATG  GGG  CAC  ATG  CTG  CAG  CGG  CCG  CTG  GTG  CTG  CAC   1103
Lys  Val  Glu  Arg  Met  Gly  His  Met  Leu  Gln  Arg  Pro  Leu  Val  Leu  His
               275                      280                     285

ACG  TCT  GCG  GCG  GCC  GAG  CTC  CCC  CGC  GCC  AAC  ACA  CAC  ATA  TAATCTTTGC  1155
Thr  Ser  Ala  Ala  Ala  Glu  Leu  Pro  Arg  Ala  Asn  Thr  His  Ile
          290                      295                     300

TATATTAAAA  CTCTATAAAC  GTATGCCACA  CGGCGCCCGC  GGGCTGCCAC  ACGCTGCTCA   1215

CGGGCTGCCG  AACAGTTCTA  ACAAGTAATC  GCGCGCCTCG  CCAGTGATCG  TGGCGAGCAC   1275

CTTGTCGTCC  ATCATCACAT  ATCCTCGGCT  ACAGTCGTCG  TTGAAGAGCG  TGCA         1329
```

( 2 ) INFORMATION FOR SEQ ID NO: 2:

( i ) SEQUENCE CHARACTERISTICS:
        ( A ) LENGTH: 301 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Thr  Glu  Tyr  Thr  Val  Pro  Glu  Val  Arg  Cys  Val  Ala  Arg  Ala  Arg
  1                 5                      10                      15

Ile  Pro  Thr  Val  Gln  Gly  Thr  Asp  Val  Phe  Leu  His  Leu  Tyr  His  Asn
               20                      25                      30

Ser  Ile  Asp  Ser  Lys  Glu  His  Leu  Ala  Ile  Val  Phe  Gly  Glu  Asn  Ile
          35                      40                      45

Arg  Ser  Arg  Ser  Leu  Phe  Arg  Tyr  Arg  Lys  Asp  Asp  Thr  Gln  Gln  Ala
     50                      55                      60

Arg  Met  Val  Arg  Gly  Ala  Tyr  Val  Gly  Gln  Leu  Tyr  Pro  Gly  Arg  Thr
 65                      70                      75                       80

Glu  Ala  Asp  Ala  Asp  Arg  Arg  Gln  Gly  Leu  Glu  Leu  Arg  Phe  Asp  Glu
                    85                      90                       95

Thr  Gly  Gln  Leu  Val  Val  Glu  Arg  Ala  Thr  Thr  Trp  Thr  Arg  Glu  Pro
```

|     |     |     |     |     | 100 |     |     |     |     | 105 |     |     |     |     | 110 |     |     |
| --- | --- | --- | --- | --- | --- | --- | --- | --- | --- | --- | --- | --- | --- | --- | --- | --- | --- |
| Thr | Leu | Val | Arg | Leu | His | Ser | Glu | Cys | Tyr | Thr | Gly | Glu | Thr | Ala | Trp |
|     |     | 115 |     |     |     |     | 120 |     |     |     |     | 125 |     |     |     |
| Ser | Ala | Arg | Cys | Asp | Cys | Gly | Glu | Gln | Phe | Asp | Gln | Ala | Gly | Lys | Leu |
|     | 130 |     |     |     |     | 135 |     |     |     |     | 140 |     |     |     |     |
| Met | Ala | Ala | Ala | Thr | Glu | Gly | Glu | Val | Val | Gly | Gly | Ala | Gly | His | Gly |
| 145 |     |     |     |     | 150 |     |     |     |     | 155 |     |     |     |     | 160 |
| Val | Ile | Val | Tyr | Leu | Arg | Gln | Glu | Gly | Arg | Gly | Ile | Gly | Leu | Gly | Glu |
|     |     |     |     | 165 |     |     |     |     | 170 |     |     |     |     | 175 |     |
| Lys | Leu | Lys | Ala | Tyr | Asn | Leu | Gln | Asp | Leu | Gly | Ala | Asp | Thr | Val | Gln |
|     |     |     | 180 |     |     |     |     | 185 |     |     |     |     | 190 |     |     |
| Ala | Asn | Glu | Leu | Leu | Asn | His | Pro | Ala | Asp | Ala | Arg | Asp | Phe | Ser | Leu |
|     |     | 195 |     |     |     |     | 200 |     |     |     |     | 205 |     |     |     |
| Gly | Arg | Ala | Ile | Leu | Leu | Asp | Leu | Gly | Ile | Glu | Asp | Ile | Arg | Leu | Leu |
|     | 210 |     |     |     |     | 215 |     |     |     |     | 220 |     |     |     |     |
| Thr | Asn | Asn | Pro | Asp | Lys | Val | Gln | Gln | Val | His | Cys | Pro | Pro | Ala | Leu |
| 225 |     |     |     |     | 230 |     |     |     |     | 235 |     |     |     |     | 240 |
| Arg | Cys | Ile | Glu | Arg | Val | Pro | Met | Val | Pro | Leu | Ser | Trp | Thr | Gln | Pro |
|     |     |     |     | 245 |     |     |     |     | 250 |     |     |     |     | 255 |     |
| Thr | Gln | Gly | Val | Arg | Ser | Arg | Glu | Leu | Asp | Gly | Tyr | Leu | Arg | Ala | Lys |
|     |     |     | 260 |     |     |     |     | 265 |     |     |     |     | 270 |     |     |
| Val | Glu | Arg | Met | Gly | His | Met | Leu | Gln | Arg | Pro | Leu | Val | Leu | His | Thr |
|     |     | 275 |     |     |     |     | 280 |     |     |     |     | 285 |     |     |     |
| Ser | Ala | Ala | Ala | Glu | Leu | Pro | Arg | Ala | Asn | Thr | His | Ile |
|     | 290 |     |     |     |     | 295 |     |     |     |     | 300 |     |

( 2 ) INFORMATION FOR SEQ ID NO: 3:

( i ) SEQUENCE CHARACTERISTICS:
  ( A ) LENGTH: 2627 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
  ( A ) ORGANISM: Ashbya gossypii ( i x ) FEATURE:
  ( A ) NAME/KEY: 5'UTR
  ( B ) LOCATION: 1..450

( i x ) FEATURE:
  ( A ) NAME/KEY: CDS
  ( B ) LOCATION: 451..2280

( i x ) FEATURE:
  ( A ) NAME/KEY: 3'UTR
  ( B ) LOCATION: 2281..2627

( x i ) SEQUENCE DESCRIPTION: SEQ ID NO: 3:

| CTGCAGGACA | ATTTAAATTA | CGATTACACG | CGGCAGCCTT | CTTGGTGCGA | CAGGATTTTG | 60 |
| TACAAGAATG | ACCCCAAGCG | GGTAAGAGTT | CATAGGTATG | CCTCGATTGA | TAGACGTTCC | 120 |
| ATTTTGAATT | ATACTGATCA | CGAACCCGTA | ACGCTCGATG | TCAGCGTTTC | ATGCCATACA | 180 |
| CAATTTGTCC | CAATGGCTAT | GCAGAATATT | TCCCCACAGA | GCACCATGGA | AATGTATGTG | 240 |
| GGAGACGTCA | CAGATATACT | ACTGATGTTG | TTCTCCAGAG | TATACTACGC | CCCTACCATA | 300 |

-continued

```
TTCGATCTTG TGGTATTGAC GATATTCCTC TGTTTGGTTT TACTGGCACT ATTCCGTTTG      360

ACGGTATAGC GCTATTCGTT CATAGTGACA CATGCGGCAC TAGCTATTCA GCGAATCCTT      420

TATAAACTGC TACTTAACGT TCGTAACACC ATG CTC AAA GGC GTT CCT GGC CTT      474
                                   Met Leu Lys Gly Val Pro Gly Leu
                                    1                   5

CTT TTT AAG GAG ACG CAA CGT CAT CTG AAA CCC AGG CTG GTT AGG ATT        522
Leu Phe Lys Glu Thr Gln Arg His Leu Lys Pro Arg Leu Val Arg Ile
        10              15                  20

ATG GAA AAC ACA TCG CAG GAT GAG AGT CGC AAA AGA CAG GTC GCT TCG        570
Met Glu Asn Thr Ser Gln Asp Glu Ser Arg Lys Arg Gln Val Ala Ser
25                  30              35                      40

AAC TTG AGC AGC GAT GCC GAT GAG GGC TCG CCG GCA GTT ACG AGG CCG        618
Asn Leu Ser Ser Asp Ala Asp Glu Gly Ser Pro Ala Val Thr Arg Pro
                45              50                      55

GTT AAA ATC ACC AAA CGC CTC AGG AAG AAG AAC CTC GGG ACA GGC GAG        666
Val Lys Ile Thr Lys Arg Leu Arg Lys Lys Asn Leu Gly Thr Gly Glu
            60              65                  70

CTA CGG GAC AAA GCA GGA TTC AAG TTG AAG GTG CAA GAC GTG AGC AAA        714
Leu Arg Asp Lys Ala Gly Phe Lys Leu Lys Val Gln Asp Val Ser Lys
        75              80                  85

AAC CGT CAC AGA CAG GTC GAT CCG GAA TAC GAA GTC GTG GTA GAT GGC        762
Asn Arg His Arg Gln Val Asp Pro Glu Tyr Glu Val Val Val Asp Gly
90              95                  100

CCG ATG CGC AAG ATC AAA CCG TAT TTC TTC ACA TAC AAG ACT TTC TGC        810
Pro Met Arg Lys Ile Lys Pro Tyr Phe Phe Thr Tyr Lys Thr Phe Cys
105                 110                 115                     120

AAG GAG CGC TGG AGA GAT CGG AAG TTG CTT GAT GTG TTT GTG GAT GAA        858
Lys Glu Arg Trp Arg Asp Arg Lys Leu Leu Asp Val Phe Val Asp Glu
                125                 130                 135

TTT CGG GAC CGC GAT AGG CCT TAC TAC GAG AAA GTC ATC GGT TCG GGT        906
Phe Arg Asp Arg Asp Arg Pro Tyr Tyr Glu Lys Val Ile Gly Ser Gly
            140                 145                 150

GGT GTG CTC CTG AAC GGT AAG TCA TCG ACG TTA GAT AGC GTA TTG CGT        954
Gly Val Leu Leu Asn Gly Lys Ser Ser Thr Leu Asp Ser Val Leu Arg
        155                 160                 165

AAT GGA GAC CTC ATT TCG CAC GAG CTG CAC CGT CAT GAG CCA CCG GTC       1002
Asn Gly Asp Leu Ile Ser His Glu Leu His Arg His Glu Pro Pro Val
    170                 175                 180

TCC TCT AGG CCG ATT AGG ACG GTG TAC GAA GAT GAT GAC ATC CTG GTG       1050
Ser Ser Arg Pro Ile Arg Thr Val Tyr Glu Asp Asp Asp Ile Leu Val
185                 190                 195                 200

ATT GAC AAG CCC AGC GGG ATT CCA GCC CAT CCC ACC GGG CGT TAC CGC       1098
Ile Asp Lys Pro Ser Gly Ile Pro Ala His Pro Thr Gly Arg Tyr Arg
                205                 210                 215

TTC AAC TCC ATT ACG AAA ATA CTT GAA AAA CAG CTT GGA TAC ACT GTT       1146
Phe Asn Ser Ile Thr Lys Ile Leu Glu Lys Gln Leu Gly Tyr Thr Val
            220                 225                 230

CAT CCA TGT AAC CGA CTG GAC CGC CTA ACC AGT GGC CTA ATG TTC TTG       1194
His Pro Cys Asn Arg Leu Asp Arg Leu Thr Ser Gly Leu Met Phe Leu
        235                 240                 245

GCA AAA ACT CCA AAG GGA GCC GAT GAG ATG GGT GAT CAG ATG AAG GCG       1242
Ala Lys Thr Pro Lys Gly Ala Asp Glu Met Gly Asp Gln Met Lys Ala
    250                 255                 260

CGC GAA GTG AAG AAA GAA TAT GTT GCC CGG GTT GTT GGG GAA TTT CCT       1290
Arg Glu Val Lys Lys Glu Tyr Val Ala Arg Val Val Gly Glu Phe Pro
265                 270                 275                 280

ATA GGT GAG ATA GTT GTG GAT ATG CCA CTG AAG ACT ATA GAG CCG AAG       1338
Ile Gly Glu Ile Val Val Asp Met Pro Leu Lys Thr Ile Glu Pro Lys
                285                 290                 295
```

| | | | | | | | | | | | | | | | | |
|---|---|---|---|---|---|---|---|---|---|---|---|---|---|---|---|---|
| CTT | GCC | CTA | AAC | ATG | GTT | TGC | GAC | CCG | GAA | GAC | GAA | GCG | GGC | AAG | GGC | 1386 |
| Leu | Ala | Leu | Asn 300 | Met | Val | Cys | Asp | Pro 305 | Glu | Asp | Glu | Ala | Gly 310 | Lys | Gly | |
| GCT | AAG | ACG | CAG | TTC | AAA | AGA | ATC | AGC | TAC | GAT | GGA | CAA | ACG | AGC | ATA | 1434 |
| Ala | Lys | Thr 315 | Gln | Phe | Lys | Arg | Ile | Ser 320 | Tyr | Asp | Gly | Gln | Thr 325 | Ser | Ile | |
| GTC | AAG | TGC | CAA | CCG | TAC | ACG | GGC | CGG | ACG | CAT | CAG | ATC | CGT | GTT | CAC | 1482 |
| Val | Lys 330 | Cys | Gln | Pro | Tyr | Thr 335 | Gly | Arg | Thr | His | Gln 340 | Ile | Arg | Val | His | |
| TTG | CAA | TAC | CTG | GGC | TTC | CCA | ATT | GCC | AAC | GAT | CCG | ATT | TAT | TCC | AAT | 1530 |
| Leu 345 | Gln | Tyr | Leu | Gly | Phe 350 | Pro | Ile | Ala | Asn | Asp 355 | Pro | Ile | Tyr | Ser | Asn 360 | |
| CCG | CAC | ATA | TGG | GGC | CCA | AGT | CTG | GGC | AAG | GAA | TGC | AAA | GCA | GAC | TAC | 1578 |
| Pro | His | Ile | Trp | Gly 365 | Pro | Ser | Leu | Gly | Lys 370 | Glu | Cys | Lys | Ala | Asp 375 | Tyr | |
| AAG | GAG | GTC | ATC | CAA | AAA | CTA | AAC | GAA | ATT | GGT | AAG | ACT | AAA | TCT | GCG | 1626 |
| Lys | Glu | Val | Ile 380 | Gln | Lys | Leu | Asn | Glu 385 | Ile | Gly | Lys | Thr | Lys 390 | Ser | Ala | |
| GAA | AGT | TGG | TAC | CAT | TCT | GAT | TCC | CAA | GGT | GAA | GTT | TTC | AAA | GGG | GAA | 1674 |
| Glu | Ser | Trp 395 | Tyr | His | Ser | Asp | Ser 400 | Gln | Gly | Glu | Val | Phe 405 | Lys | Gly | Glu | |
| CAA | TGC | GAT | GAA | TGT | GGC | ACC | GAA | CTG | TAC | ACT | GAC | CCG | GGC | CCG | AAT | 1722 |
| Gln | Cys 410 | Asp | Glu | Cys | Gly | Thr 415 | Glu | Leu | Tyr | Thr | Asp 420 | Pro | Gly | Pro | Asn | |
| GAT | CTT | GAC | TTA | TGG | TTG | CAT | GCA | TAT | CGG | TAT | GAA | TCC | ACT | GAA | CTG | 1770 |
| Asp 425 | Leu | Asp | Leu | Trp | Leu 430 | His | Ala | Tyr | Arg | Tyr 435 | Glu | Ser | Thr | Glu | Leu 440 | |
| GAT | GAG | AAC | GGT | GCT | AAA | AAG | CGG | AGT | TAC | TCT | ACT | GCG | TTT | CCT | GAG | 1818 |
| Asp | Glu | Asn | Gly | Ala 445 | Lys | Lys | Arg | Ser | Tyr 450 | Ser | Thr | Ala | Phe | Pro 455 | Glu | |
| TGG | GCT | CTT | GAG | CAG | CAC | GGC | GAC | TTC | ATG | CGG | CTT | GCC | ATC | GAA | CAG | 1866 |
| Trp | Ala | Leu | Glu 460 | Gln | His | Gly | Asp | Phe 465 | Met | Arg | Leu | Ala | Ile 470 | Glu | Gln | |
| GCT | AAG | AAA | TGC | CCA | CCC | GCG | AAG | ACA | TCA | TTT | AGC | GTT | GGT | GCC | GTG | 1914 |
| Ala | Lys | Lys 475 | Cys | Pro | Pro | Ala | Lys 480 | Thr | Ser | Phe | Ser | Val 485 | Gly | Ala | Val | |
| TTA | GTT | AAT | GGG | ACC | GAG | ATT | TTG | GCC | ACT | GGT | TAC | TCA | CGG | GAG | CTG | 1962 |
| Leu | Val 490 | Asn | Gly | Thr | Glu | Ile 495 | Leu | Ala | Thr | Gly | Tyr 500 | Ser | Arg | Glu | Leu | |
| GAA | GGC | AAC | ACG | CAC | GCT | GAA | CAA | TGT | GCA | CTT | CAA | AAA | TAT | TTT | GAA | 2010 |
| Glu 505 | Gly | Asn | Thr | His | Ala 510 | Glu | Gln | Cys | Ala | Leu 515 | Gln | Lys | Tyr | Phe | Glu 520 | |
| CAA | CAT | AAA | ACC | GAC | AAG | GTT | CCT | ATT | GGT | ACA | GTA | ATA | TAC | ACG | ACT | 2058 |
| Gln | His | Lys | Thr | Asp 525 | Lys | Val | Pro | Ile | Gly 530 | Thr | Val | Ile | Tyr | Thr 535 | Thr | |
| ATG | GAG | CCT | TGT | TCT | CTC | CGT | CTC | AGT | GGT | AAT | AAA | CCG | TGT | GTT | GAG | 2106 |
| Met | Glu | Pro | Cys 540 | Ser | Leu | Arg | Leu | Ser 545 | Gly | Asn | Lys | Pro | Cys 550 | Val | Glu | |
| CGT | ATA | ATC | TGC | CAG | CAG | GGT | AAT | ATT | ACT | GCT | GTT | TTT | GTT | GGC | GTA | 2154 |
| Arg | Ile | Ile 555 | Cys | Gln | Gln | Gly | Asn 560 | Ile | Thr | Ala | Val | Phe 565 | Val | Gly | Val | |
| CTT | GAG | CCA | GAC | AAC | TTC | GTG | AAG | AAC | AAT | ACA | AGT | CGT | GCG | CTA | TTG | 2202 |
| Leu | Glu 570 | Pro | Asp | Asn | Phe | Val 575 | Lys | Asn | Asn | Thr | Ser 580 | Arg | Ala | Leu | Leu | |
| GAA | CAA | CAT | GGT | ATA | GAC | TAT | ATT | CTT | GTC | CCT | GGG | TTT | CAA | GAA | GAA | 2250 |
| Glu 585 | Gln | His | Gly | Ile | Asp 590 | Tyr | Ile | Leu | Val | Pro 595 | Gly | Phe | Gln | Glu | Glu 600 | |
| TGT | ACT | GAA | GCC | GCA | TTG | AAG | GGT | CAT | TGATTTTGCT | | | GCGAATTGTA | | | | 2297 |
| Cys | Thr | Glu | Ala | Ala 605 | Leu | Lys | Gly | His 610 | | | | | | | | |

| | | | | |
|---|---|---|---|---|
| GATGACTTAA AATATCGAGG CGTATAATTC GTCGCATTTT ATATAGTTAT CTATGTTTAC | | | | | 2357 |
| ATGACTGTTT AAGCTTGATC TATATTTCTC AAGTGAATTG CCACATATGT TGGTACGGTA | | | | | 2417 |
| ATAAATTAAT GAGGGAGTTT TGAAATTCGC AACCAATCTT ATATACGTTT GATGATATAA | | | | | 2477 |
| ACGGATTGAG ATTCATTAAG CTACCTGATT TTCGCTGAAC TGTTTGTTAT AGGTTTTTAC | | | | | 2537 |
| AGTAAGATAG TTCCTAAGTT TGTTTATTGT CCCCAGTCGG CCAATTGTTC CGGACTTATT | | | | | 2597 |
| ATTATTACCA TTAGTGGTGT TAGTAGTATT | | | | | 2627 |

( 2 ) INFORMATION FOR SEQ ID NO: 4:

( i ) SEQUENCE CHARACTERISTICS:
        ( A ) LENGTH: 609 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Met Leu Lys Gly Val Pro Gly Leu Leu Phe Lys Glu Thr Gln Arg His
 1               5                  10                  15
Leu Lys Pro Arg Leu Val Arg Ile Met Glu Asn Thr Ser Gln Asp Glu
                20                  25                  30
Ser Arg Lys Arg Gln Val Ala Ser Asn Leu Ser Ser Asp Ala Asp Glu
            35                  40                  45
Gly Ser Pro Ala Val Thr Arg Pro Val Lys Ile Thr Lys Arg Leu Arg
        50                  55                  60
Lys Lys Asn Leu Gly Thr Gly Glu Leu Arg Asp Lys Ala Gly Phe Lys
 65                  70                  75                  80
Leu Lys Val Gln Asp Val Ser Lys Asn Arg His Arg Gln Val Asp Pro
                85                  90                  95
Glu Tyr Glu Val Val Val Asp Gly Pro Met Arg Lys Ile Lys Pro Tyr
           100                 105                 110
Phe Phe Thr Tyr Lys Thr Phe Cys Lys Glu Arg Trp Arg Asp Arg Lys
           115                 120                 125
Leu Leu Asp Val Phe Val Asp Glu Phe Arg Asp Arg Asp Arg Pro Tyr
       130                 135                 140
Tyr Glu Lys Val Ile Gly Ser Gly Gly Val Leu Leu Asn Gly Lys Ser
145                 150                 155                 160
Ser Thr Leu Asp Ser Val Leu Arg Asn Gly Asp Leu Ile Ser His Glu
               165                 170                 175
Leu His Arg His Glu Pro Pro Val Ser Ser Arg Pro Ile Arg Thr Val
           180                 185                 190
Tyr Glu Asp Asp Asp Ile Leu Val Ile Asp Lys Pro Ser Gly Ile Pro
       195                 200                 205
Ala His Pro Thr Gly Arg Tyr Arg Phe Asn Ser Ile Thr Lys Ile Leu
   210                 215                 220
Glu Lys Gln Leu Gly Tyr Thr Val His Pro Cys Asn Arg Leu Asp Arg
225                 230                 235                 240
Leu Thr Ser Gly Leu Met Phe Leu Ala Lys Thr Pro Lys Gly Ala Asp
               245                 250                 255
Glu Met Gly Asp Gln Met Lys Ala Arg Glu Val Lys Lys Glu Tyr Val
           260                 265                 270
Ala Arg Val Val Gly Glu Phe Pro Ile Gly Glu Ile Val Val Asp Met
       275                 280                 285
Pro Leu Lys Thr Ile Glu Pro Lys Leu Ala Leu Asn Met Val Cys Asp
   290                 295                 300
```

| | | | | | | | | | | | | | | |
|---|---|---|---|---|---|---|---|---|---|---|---|---|---|---|
| Pro<br>305 | Glu | Asp | Glu | Ala | Gly<br>310 | Lys | Gly | Ala | Lys<br>315 | Thr | Gln | Phe | Lys | Arg | Ile<br>320 |
| Ser | Tyr | Asp | Gly | Gln<br>325 | Thr | Ser | Ile | Val | Lys<br>330 | Cys | Gln | Pro | Tyr | Thr<br>335 | Gly |
| Arg | Thr | His | Gln<br>340 | Ile | Arg | Val | His | Leu<br>345 | Gln | Tyr | Leu | Gly | Phe<br>350 | Pro | Ile |
| Ala | Asn | Asp<br>355 | Pro | Ile | Tyr | Ser | Asn<br>360 | Pro | His | Ile | Trp | Gly<br>365 | Pro | Ser | Leu |
| Gly | Lys<br>370 | Glu | Cys | Lys | Ala | Asp<br>375 | Tyr | Lys | Glu | Val | Ile<br>380 | Gln | Lys | Leu | Asn |
| Glu<br>385 | Ile | Gly | Lys | Thr | Lys<br>390 | Ser | Ala | Glu | Ser | Trp<br>395 | Tyr | His | Ser | Asp | Ser<br>400 |
| Gln | Gly | Glu | Val | Phe<br>405 | Lys | Gly | Glu | Gln | Cys<br>410 | Asp | Glu | Cys | Gly | Thr<br>415 | Glu |
| Leu | Tyr | Thr | Asp<br>420 | Pro | Gly | Pro | Asn | Asp<br>425 | Leu | Asp | Leu | Trp | Leu<br>430 | His | Ala |
| Tyr | Arg | Tyr<br>435 | Glu | Ser | Thr | Glu | Leu<br>440 | Asp | Glu | Asn | Gly | Ala<br>445 | Lys | Lys | Arg |
| Ser | Tyr<br>450 | Ser | Thr | Ala | Phe | Pro<br>455 | Glu | Trp | Ala | Leu | Glu<br>460 | Gln | His | Gly | Asp |
| Phe<br>465 | Met | Arg | Leu | Ala | Ile<br>470 | Glu | Gln | Ala | Lys | Lys<br>475 | Cys | Pro | Pro | Ala | Lys<br>480 |
| Thr | Ser | Phe | Ser | Val<br>485 | Gly | Ala | Val | Leu | Val<br>490 | Asn | Gly | Thr | Glu | Ile<br>495 | Leu |
| Ala | Thr | Gly | Tyr<br>500 | Ser | Arg | Glu | Leu | Glu<br>505 | Gly | Asn | Thr | His | Ala<br>510 | Glu | Gln |
| Cys | Ala | Leu<br>515 | Gln | Lys | Tyr | Phe | Glu<br>520 | Gln | His | Lys | Thr | Asp<br>525 | Lys | Val | Pro |
| Ile | Gly | Thr<br>530 | Val | Ile | Tyr | Thr | Thr<br>535 | Met | Glu | Pro | Cys | Ser<br>540 | Leu | Arg | Leu |
| Ser<br>545 | Gly | Asn | Lys | Pro | Cys<br>550 | Val | Glu | Arg | Ile | Ile<br>555 | Cys | Gln | Gln | Gly | Asn<br>560 |
| Ile | Thr | Ala | Val | Phe<br>565 | Val | Gly | Val | Leu | Glu<br>570 | Pro | Asp | Asn | Phe | Val<br>575 | Lys |
| Asn | Asn | Thr | Ser<br>580 | Arg | Ala | Leu | Leu | Glu<br>585 | Gln | His | Gly | Ile | Asp<br>590 | Tyr | Ile |
| Leu | Val | Pro<br>595 | Gly | Phe | Gln | Glu | Glu<br>600 | Cys | Thr | Glu | Ala | Ala<br>605 | Leu | Lys | Gly |
| His | | | | | | | | | | | | | | | |

( 2 ) INFORMATION FOR SEQ ID NO: 5:

( i ) SEQUENCE CHARACTERISTICS:
        ( A ) LENGTH: 1082 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Ashbya gossypii ( i x ) FEATURE:
        ( A ) NAME/KEY: 5'UTR

5,821,090

-continued ( B ) LOCATION: 1..314

( i x ) FEATURE:
    ( A ) NAME/KEY: CDS
    ( B ) LOCATION: 315..953

( i x ) FEATURE:
    ( A ) NAME/KEY: 3'UTR
    ( B ) LOCATION: 954..1082

( x i ) SEQUENCE DESCRIPTION: SEQ ID NO: 5:

```
CCCTTCTTGC ACGGTCGTTT CTGAAACTCT ACGATTATTG GAACAATGAG TAAGTCCTCA        60

AATGTACCAC CTATCTGTAG TTTACTATCG GATTTACTGG CTAAGAGCTG ACCTGTTAGG       120

CAAGTGAAAC ATATCACATC GCCAGCAGGT TGGGCTACCA AGGATAGTTG ATGACTTCCA       180

TCACCTATAA AAGCGGCTTG AGTGCTTTTG CAATGATTCT GTTCACATGA TGGACAAGAA       240

ATACGTACAA AAATTTCAAC GTTTTACAAG TTCCCAAGCT TAGTCAACTC ATCACCAACG       300

ACAAACCAAG CAAC ATG ACA AGC CCA TGC ACT GAT ATC GGT ACC GCT ATA        350
              Met Thr Ser Pro Cys Thr Asp Ile Gly Thr Ala Ile
                1               5                  10

GAG CAG TTC AAG CAA AAT AAG ATG ATC ATC GTC ATG GAC CAC ATC TCG        398
Glu Gln Phe Lys Gln Asn Lys Met Ile Ile Val Met Asp His Ile Ser
             15                  20                  25

AGA GAA AAC GAG GCC GAT CTA ATA TGT GCA GCA GCG CAC ATG ACT GCC        446
Arg Glu Asn Glu Ala Asp Leu Ile Cys Ala Ala Ala His Met Thr Ala
        30                  35                  40

GAG CAA ATG GCA TTT ATG ATT CGG TAT TCC TCG GGC TAC GTT TGC GCT        494
Glu Gln Met Ala Phe Met Ile Arg Tyr Ser Ser Gly Tyr Val Cys Ala
45                  50                  55                  60

CCA ATG ACC AAT GCG ATT GCC GAT AAG CTA GAC CTA CCG CTC ATG AAC        542
Pro Met Thr Asn Ala Ile Ala Asp Lys Leu Asp Leu Pro Leu Met Asn
                65                  70                  75

ACA TTG AAA TGC AAG GCT TTC TCC GAT GAC AGA CAC AGC ACT GCG TAT        590
Thr Leu Lys Cys Lys Ala Phe Ser Asp Asp Arg His Ser Thr Ala Tyr
            80                  85                  90

ACA ATC ACC TGT GAC TAT GCG CAC GGG ACG ACG ACA GGT ATC TCC GCA        638
Thr Ile Thr Cys Asp Tyr Ala His Gly Thr Thr Thr Gly Ile Ser Ala
        95                  100                 105

CGT GAC CGG GCG TTG ACC GTG AAT CAG TTG GCG AAC CCG GAG TCC AAG        686
Arg Asp Arg Ala Leu Thr Val Asn Gln Leu Ala Asn Pro Glu Ser Lys
    110                 115                 120

GCT ACC GAC TTC ACG AAG CCA GGC CAC ATT GTG CCA TTG CGT GCC CGT        734
Ala Thr Asp Phe Thr Lys Pro Gly His Ile Val Pro Leu Arg Ala Arg
125                 130                 135                 140

GAC GGC GGC GTG CTC GAG CGT GAC GGG CAC ACC GAA GCG GCG CTC GAC        782
Asp Gly Gly Val Leu Glu Arg Asp Gly His Thr Glu Ala Ala Leu Asp
                145                 150                 155

TTG TGC AGA CTA GCG GGT GTG CCA GAG GTC GCT GCT ATT TGT GAA TTA        830
Leu Cys Arg Leu Ala Gly Val Pro Glu Val Ala Ala Ile Cys Glu Leu
            160                 165                 170

GTA AGC GAA AGG GAC GTC GGG CTG ATG ATG ACT TTG GAT GAG TGT ATA        878
Val Ser Glu Arg Asp Val Gly Leu Met Met Thr Leu Asp Glu Cys Ile
        175                 180                 185

GAA TTC AGC AAG AAG CAC GGT CTT GCC CTC ATC ACC GTG CAT GAC CTG        926
Glu Phe Ser Lys Lys His Gly Leu Ala Leu Ile Thr Val His Asp Leu
    190                 195                 200

AAG GCT GCA GTT GCC GCC AAG CAG TAGACGGCAA CGAGTTCTTT AAGTCGGTGT        980
Lys Ala Ala Val Ala Ala Lys Gln
205                 210

TCATTTATGT AATATACCAT TTCATCGAAA AAGTCAAATG GTATGAACTA GATTTATCAA      1040
```

TAGTATCTAA GAGTTATGGT ATTCGCAAAA GCTTATCGAT AC                            1082

( 2 ) INFORMATION FOR SEQ ID NO: 6:

( i ) SEQUENCE CHARACTERISTICS:
        ( A ) LENGTH: 212 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Met Thr Ser Pro Cys Thr Asp Ile Gly Thr Ala Ile Glu Gln Phe Lys
 1               5                  10                      15

Gln Asn Lys Met Ile Ile Val Met Asp His Ile Ser Arg Glu Asn Glu
            20                  25                  30

Ala Asp Leu Ile Cys Ala Ala Ala His Met Thr Ala Glu Gln Met Ala
            35                  40                  45

Phe Met Ile Arg Tyr Ser Ser Gly Tyr Val Cys Ala Pro Met Thr Asn
        50                  55                  60

Ala Ile Ala Asp Lys Leu Asp Leu Pro Leu Met Asn Thr Leu Lys Cys
 65                 70                  75                      80

Lys Ala Phe Ser Asp Asp Arg His Ser Thr Ala Tyr Thr Ile Thr Cys
                85                  90                  95

Asp Tyr Ala His Gly Thr Thr Thr Gly Ile Ser Ala Arg Asp Arg Ala
               100                 105                 110

Leu Thr Val Asn Gln Leu Ala Asn Pro Glu Ser Lys Ala Thr Asp Phe
           115                 120                 125

Thr Lys Pro Gly His Ile Val Pro Leu Arg Ala Arg Asp Gly Gly Val
    130                 135                 140

Leu Glu Arg Asp Gly His Thr Glu Ala Ala Leu Asp Leu Cys Arg Leu
145                 150                 155                 160

Ala Gly Val Pro Glu Val Ala Ala Ile Cys Glu Leu Val Ser Glu Arg
                165                 170                 175

Asp Val Gly Leu Met Met Thr Leu Asp Glu Cys Ile Glu Phe Ser Lys
            180                 185                 190

Lys His Gly Leu Ala Leu Ile Thr Val His Asp Leu Lys Ala Ala Val
            195                 200                 205

Ala Ala Lys Gln
    210
```

( 2 ) INFORMATION FOR SEQ ID NO: 7:

( i ) SEQUENCE CHARACTERISTICS:
        ( A ) LENGTH: 996 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Ashbya gossypii ( i x ) FEATURE:
        ( A ) NAME/KEY: 5'UTR
        ( B ) LOCATION: 1..270

( i x ) FEATURE:
        ( A ) NAME/KEY: CDS (B) LOCATION: 271..789

(ix) FEATURE:
    (A) NAME/KEY: 3'UTR
    (B) LOCATION: 790..996

(xi) SEQUENCE DESCRIPTION: SEQ ID NO: 7:

```
TGGTATAATG ATACAGGAAG TGAAAATCCG AAAGGTTCAG ACGATGAAAA GAGTTTGAGA        60

CGCATCAATG ATCAGCTTTG AGCTATATGT AAGTCTATTA ATTGATTACT AATAGCAATT       120

TATGGTATCC TCTGTTCTGC ATATCGACGG TTCTCACGTG ATGATCAGCT TGAGGCTTCG       180

CGGATAAAGT TCCATCGATT ACTATAAAAC CATCACATTA AACGTTCACT ATAGGCATAC       240

ACACAGACTA AGTTCAAGTT AGCAGTGACA ATG ATT AAG GGA TTA GGC GAA GTT        294
                                 Met Ile Lys Gly Leu Gly Glu Val
                                   1               5

GAT CAA ACC TAC GAT GCG AGC TCT GTC GAG GTT GGC ATT GTC CAC GCG         342
Asp Gln Thr Tyr Asp Ala Ser Ser Val Glu Val Gly Ile Val His Ala
        10                  15                  20

AGA TGG AAC AAG ACT GTC ATT GAC GCT CTC GAC CAA GGT GCA ATT GAG         390
Arg Trp Asn Lys Thr Val Ile Asp Ala Leu Asp Gln Gly Ala Ile Glu
 25                  30                  35                  40

AAA CTG CTT GCT ATG GGA GTG AAG GAG AAG AAT ATC ACT GTA AGC ACC         438
Lys Leu Leu Ala Met Gly Val Lys Glu Lys Asn Ile Thr Val Ser Thr
                     45                  50                  55

GTT CCA GGT GCG TTT GAA CTA CCA TTT GGC ACT CAG CGG TTT GCC GAG         486
Val Pro Gly Ala Phe Glu Leu Pro Phe Gly Thr Gln Arg Phe Ala Glu
            60                  65                  70

CTG ACC AAG GCA AGT GGC AAG CAT TTG GAC GTG GTC ATC CCA ATT GGA         534
Leu Thr Lys Ala Ser Gly Lys His Leu Asp Val Val Ile Pro Ile Gly
        75                  80                  85

GTC CTG ATC AAA GGC GAC TCA ATG CAC TTT GAA TAT ATA TCA GAC TCT         582
Val Leu Ile Lys Gly Asp Ser Met His Phe Glu Tyr Ile Ser Asp Ser
 90                  95                 100

GTG ACT CAT GCC TTA ATG AAC CTA CAG AAG AAG ATT CGT CTT CCT GTC         630
Val Thr His Ala Leu Met Asn Leu Gln Lys Lys Ile Arg Leu Pro Val
105                 110                 115                 120

ATT TTT GGT TTG CTA ACG TGT CTA ACA GAG GAA CAA GCG TTG ACA CGT         678
Ile Phe Gly Leu Leu Thr Cys Leu Thr Glu Glu Gln Ala Leu Thr Arg
                    125                 130                 135

GCA GGC CTC GGT GAA TCT GAA GGC AAG CAC AAC CAC GGT GAA GAC TGG         726
Ala Gly Leu Gly Glu Ser Glu Gly Lys His Asn His Gly Glu Asp Trp
            140                 145                 150

GGT GCT GCT GCC GTG GAG ATG GCT GTA AAG TTT GGC CCA CGC GCC GAA         774
Gly Ala Ala Ala Val Glu Met Ala Val Lys Phe Gly Pro Arg Ala Glu
        155                 160                 165

CAA ATG AAG AAG TGAATATTAA AAAATCACTA CTTAAAATTA ACGTTTTTAT             826
Gln Met Lys Lys
170

TATGTCTATA TCAAATTCTT ACGTGATAAC TTTTGATTTC GCTTCCTGGA TTGGCGCAAG       886

GCCTCCCTGT GTCGCAGTTT TTGTTCACGG GTCCACACAG CTCTGTTTTC CCAGAACATA       946

TCCTCCCAGC CGGCGAACCG GTTAGACGCT TCTGCTGGCG TTCTTATTTT                  996
```

(2) INFORMATION FOR SEQ ID NO: 8:

(i) SEQUENCE CHARACTERISTICS:
        (A) LENGTH: 172 amino acids
        (B) TYPE: amino acid
        (D) TOPOLOGY: linear (ii) MOLECULE TYPE: protein ( x i ) SEQUENCE DESCRIPTION: SEQ ID NO: 8:

| Met | Ile | Lys | Gly | Leu | Gly | Glu | Val | Asp | Gln | Thr | Tyr | Asp | Ala | Ser | Ser |
| 1 | | | | 5 | | | | | 10 | | | | | 15 | |

| Val | Glu | Val | Gly | Ile | Val | His | Ala | Arg | Trp | Asn | Lys | Thr | Val | Ile | Asp |
| | | | 20 | | | | | 25 | | | | | 30 | | |

| Ala | Leu | Asp | Gln | Gly | Ala | Ile | Glu | Lys | Leu | Leu | Ala | Met | Gly | Val | Lys |
| | | 35 | | | | | 40 | | | | | 45 | | | |

| Glu | Lys | Asn | Ile | Thr | Val | Ser | Thr | Val | Pro | Gly | Ala | Phe | Glu | Leu | Pro |
| | 50 | | | | | 55 | | | | | 60 | | | | |

| Phe | Gly | Thr | Gln | Arg | Phe | Ala | Glu | Leu | Thr | Lys | Ala | Ser | Gly | Lys | His |
| 65 | | | | | 70 | | | | | 75 | | | | | 80 |

| Leu | Asp | Val | Val | Ile | Pro | Ile | Gly | Val | Leu | Ile | Lys | Gly | Asp | Ser | Met |
| | | | | 85 | | | | | 90 | | | | | 95 | |

| His | Phe | Glu | Tyr | Ile | Ser | Asp | Ser | Val | Thr | His | Ala | Leu | Met | Asn | Leu |
| | | | 100 | | | | | 105 | | | | | 110 | | |

| Gln | Lys | Lys | Ile | Arg | Leu | Pro | Val | Ile | Phe | Gly | Leu | Leu | Thr | Cys | Leu |
| | | 115 | | | | | 120 | | | | | 125 | | | |

| Thr | Glu | Glu | Gln | Ala | Leu | Thr | Arg | Ala | Gly | Leu | Gly | Glu | Ser | Glu | Gly |
| | 130 | | | | | 135 | | | | | 140 | | | | |

| Lys | His | Asn | His | Gly | Glu | Asp | Trp | Gly | Ala | Ala | Ala | Val | Glu | Met | Ala |
| 145 | | | | | 150 | | | | | 155 | | | | | 160 |

| Val | Lys | Phe | Gly | Pro | Arg | Ala | Glu | Gln | Met | Lys | Lys |
| | | | | 165 | | | | | 170 | | |

( 2 ) INFORMATION FOR SEQ ID NO: 9:

( i ) SEQUENCE CHARACTERISTICS:
        ( A ) LENGTH: 1511 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Ashbya gossypii ( i x ) FEATURE:
        ( A ) NAME/KEY: 5'UTR
        ( B ) LOCATION: 1..524

( i x ) FEATURE:
        ( A ) NAME/KEY: CDS
        ( B ) LOCATION: 525..1232

( i x ) FEATURE:
        ( A ) NAME/KEY: 3'UTR
        ( B ) LOCATION: 1233..1511

( x i ) SEQUENCE DESCRIPTION: SEQ ID NO: 9:

| TGTATTCAAC | CTGGAGGATA | ACGAAATTTC | CATGGCGCGG | GCGATACCAA | CCCACAGGAG | 60 |
| CCAGATATAA | GACCAATCCC | GGCGGGTGTG | CCAGCCGCCA | TCAGAGACAG | CGGGCCAGCA | 120 |
| AGGCATGTGA | AGTCAAAAGG | CGCCAGCTCC | TTATCCGCTC | CCGCACAAGC | AGGACCGGCA | 180 |
| TATCCCGATG | AGCGCGCCAG | CACCCAGACG | CTACACCACC | ATTCGAAGTA | GACTTTAAAA | 240 |
| GAGCGCTTTC | CAGCTTCTCA | GGCAGTTAGC | TCTACGACAA | AGGAACCAAG | TGATTTTCCC | 300 |
| GATAGACGCG | ACTTGCTCAA | CGATGTTTCT | GTGACCAGCG | CAAGGAGAGA | TAGTCCTAAA | 360 |
| GTATAATCAG | ATAGTTAGTC | GTATCTTCTA | GTTTTATTAG | TCAGCTACAT | GGCGAACCGC | 420 |

```
CATTTCCTTA TGCATGTCTT ACGAGTTTAA AAAGCTCGCG GTAGCAGAAA AGAAGATGCA        480

TAGATGGCAT ACCGAAGCCT ATATCGCCCA TAGAAGTTGA TAGG ATG TTT ACC GGT        536
                                              Met Phe Thr Gly
                                               1

ATA GTG GAA CAC ATT GGC ACT GTT GCT GAG TAC TTG GAG AAC GAT GCC         584
Ile Val Glu His Ile Gly Thr Val Ala Glu Tyr Leu Glu Asn Asp Ala
 5               10                  15                      20

AGC GAG GCA GGC GGC AAC GGT GTG TCA GTC CTT ATC AAG GAT GCG GCT         632
Ser Glu Ala Gly Gly Asn Gly Val Ser Val Leu Ile Lys Asp Ala Ala
                 25                  30                      35

CCG ATA CTG GCG GAT TGC CAC ATC GGT GAC TCG ATT GCA TGC AAT GGT         680
Pro Ile Leu Ala Asp Cys His Ile Gly Asp Ser Ile Ala Cys Asn Gly
             40                  45                      50

ATC TGC CTG ACG GTG ACG GAG TTC ACG GCC GAT AGC TTC AAG GTC GGG         728
Ile Cys Leu Thr Val Thr Glu Phe Thr Ala Asp Ser Phe Lys Val Gly
         55                  60                      65

ATC GCA CCA GAA ACA GTT TAT CGG ACG GAA GTC AGC AGC TGG AAA GCT         776
Ile Ala Pro Glu Thr Val Tyr Arg Thr Glu Val Ser Ser Trp Lys Ala
     70                  75                      80

GGC TCC AAG ATC AAC CTA GAA AGG GCC ATC TCG GAC GAC AGG CGC TAC         824
Gly Ser Lys Ile Asn Leu Glu Arg Ala Ile Ser Asp Asp Arg Arg Tyr
 85                  90                      95                 100

GGC GGG CAC TAC GTG CAG GGC CAC GTC GAC TCG GTG GCC TCT ATT GTA         872
Gly Gly His Tyr Val Gln Gly His Val Asp Ser Val Ala Ser Ile Val
                 105                 110                     115

TCC AGA GAG CAC GAC GGG AAC TCT ATC AAC TTT AAG TTT AAA CTG CGC         920
Ser Arg Glu His Asp Gly Asn Ser Ile Asn Phe Lys Phe Lys Leu Arg
             120                 125                     130

GAT CAA GAG TAC GAG AAG TAC GTA GTA GAA AAG GGT TTT GTG GCG ATC         968
Asp Gln Glu Tyr Glu Lys Tyr Val Val Glu Lys Gly Phe Val Ala Ile
         135                 140                     145

GAC GGT GTG TCG CTG ACT GTA AGC AAG ATG GAT CCA GAT GGC TGT TTC        1016
Asp Gly Val Ser Leu Thr Val Ser Lys Met Asp Pro Asp Gly Cys Phe
     150                 155                     160

TAC ATC TCG ATG ATT GCA CAC ACG CAG ACC GCT GTA GCC CTT CCA CTG        1064
Tyr Ile Ser Met Ile Ala His Thr Gln Thr Ala Val Ala Leu Pro Leu
165                 170                     175                 180

AAG CCG GAC GGT GCC CTC GTG AAC ATA GAA ACG GAT GTT AAC GGC AAG        1112
Lys Pro Asp Gly Ala Leu Val Asn Ile Glu Thr Asp Val Asn Gly Lys
                 185                 190                     195

CTA GTA GAG AAG CAG GTT GCA CAG TAC CTG AAT GCG CAG CTG GAA GGT        1160
Leu Val Glu Lys Gln Val Ala Gln Tyr Leu Asn Ala Gln Leu Glu Gly
             200                 205                     210

GAG AGC TCG CCA TTG CAG CGC GTG CTC GAA AGG ATT ATT GAA TCC AAG        1208
Glu Ser Ser Pro Leu Gln Arg Val Leu Glu Arg Ile Ile Glu Ser Lys
         215                 220                     225

CTT GCT AGC ATC TCA AAT AAG TGATTATATT ATCTTGGGTG CTGTATATCT           1259
Leu Ala Ser Ile Ser Asn Lys
     230                 235

TATGTATGTC TTACGACTGT GAATCAGAGG GGTGGCAGCT GGAACACCAG CGACACACCT      1319

TCGTCTCCCG CGGTGATCAG CCTTCTGTTT TCCTCAAGTA GTACAAAGTC TAGGACACCC      1379

TGTTGTGGCC AACGCAAACA TGGAGCTGCT GCCCGTTACG CACGTCGAAC TCGTAGACCT      1439

TGCCGTCAAT GCACGAGGCG AACAGGTGGA AACCGGTGGT CTTGTCAAAC CGCCAGCTTC      1499

GTGACCGAGT CC                                                         1511
```

( 2 ) INFORMATION FOR SEQ ID NO: 10:

( i ) SEQUENCE CHARACTERISTICS:
    ( A ) LENGTH: 235 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 10:

```
Met Phe Thr Gly Ile Val Glu His Ile Gly Thr Val Ala Glu Tyr Leu
 1           5                  10                 15
Glu Asn Asp Ala Ser Glu Ala Gly Gly Asn Gly Val Ser Val Leu Ile
            20                 25                 30
Lys Asp Ala Ala Pro Ile Leu Ala Asp Cys His Ile Gly Asp Ser Ile
            35                 40                 45
Ala Cys Asn Gly Ile Cys Leu Thr Val Thr Glu Phe Thr Ala Asp Ser
        50                 55                 60
Phe Lys Val Gly Ile Ala Pro Glu Thr Val Tyr Arg Thr Glu Val Ser
 65                 70                 75                 80
Ser Trp Lys Ala Gly Ser Lys Ile Asn Leu Glu Arg Ala Ile Ser Asp
                85                 90                 95
Asp Arg Arg Tyr Gly Gly His Tyr Val Gln Gly His Val Asp Ser Val
           100                105                110
Ala Ser Ile Val Ser Arg Glu His Asp Gly Asn Ser Ile Asn Phe Lys
        115                120                125
Phe Lys Leu Arg Asp Gln Glu Tyr Glu Lys Tyr Val Val Glu Lys Gly
130                135                140
Phe Val Ala Ile Asp Gly Val Ser Leu Thr Val Ser Lys Met Asp Pro
145                150                155                160
Asp Gly Cys Phe Tyr Ile Ser Met Ile Ala His Thr Gln Thr Ala Val
               165                170                175
Ala Leu Pro Leu Lys Pro Asp Gly Ala Leu Val Asn Ile Glu Thr Asp
           180                185                190
Val Asn Gly Lys Leu Val Glu Lys Gln Val Ala Gln Tyr Leu Asn Ala
       195                200                205
Gln Leu Glu Gly Glu Ser Ser Pro Leu Gln Arg Val Leu Glu Arg Ile
   210                215                220
Ile Glu Ser Lys Leu Ala Ser Ile Ser Asn Lys
225                230                235
```

( 2 ) INFORMATION FOR SEQ ID NO: 11:

( i ) SEQUENCE CHARACTERISTICS:
        ( A ) LENGTH: 1596 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Ashbya gossypii ( i x ) FEATURE:
        ( A ) NAME/KEY: 5'UTR
        ( B ) LOCATION: 1..352

( i x ) FEATURE:
        ( A ) NAME/KEY: CDS
        ( B ) LOCATION: 353..1093

( i x ) FEATURE:
   ( A ) NAME/KEY: 3'UTR
   ( B ) LOCATION: 1094..1596

( x i ) SEQUENCE DESCRIPTION: SEQ ID NO: 11:

| | | | | | |
|---|---|---|---|---|---|
| AGAAGAAGCG | CAGGCGCCAG | TCCGAGCTGG | AGGAGAACGA | GGCGGCGCGG | TTGACGAACA | 60 |
| GCGCGCTGCC | CATGGACGAT | GCGGGTATAC | AGACGGCGGG | TATACAGACG | GCGGGTGGTG | 120 |
| CCGAGAGAGG | CACCAGGCCG | GCTTCCTCCA | GCGATGCAAG | GAAGAGAAGG | GGACCAGAGG | 180 |
| CGAAGTTCAA | GCCATCTAAG | GTACAGAAGC | CCCAATTGAA | GCGAACTGCA | TCGTCCCGGG | 240 |
| CGGATGAGAA | CGAGTTCTCG | ATATTATAGA | GGCCCCCGTT | TCGAGTGATT | GGCGTCAAAA | 300 |
| ACGGCTATCT | GCCTTCGTCC | GCCCCCACCA | CCCTCGGGAA | CACTGGCAAA | CC ATG      | 355 |

|     |     |     |     |     |     |     |     |     |     |     |     |     |     |     |     |     |
|---|---|---|---|---|---|---|---|---|---|---|---|---|---|---|---|---|
|     |     |     |     |     |     |     |     |     |     |     |     |     |     |     |     | Met |
|     |     |     |     |     |     |     |     |     |     |     |     |     |     |     |     | 1   |
| GCG | CTA | ATA | CCA | CTT | TCT | CAA | GAT | CTG | GCT | GAT | ATA | CTA | GCA | CCG | TAC | 403 |
| Ala | Leu | Ile | Pro | Leu | Ser | Gln | Asp | Leu | Ala | Asp | Ile | Leu | Ala | Pro | Tyr |     |
|     |     |     |     | 5   |     |     |     | 10  |     |     |     | 15  |     |     |     |     |
| TTA | CCG | ACA | CCA | CCG | GAC | TCA | TCC | GCA | CGC | CTG | CCG | TTT | GTC | ACG | CTG | 451 |
| Leu | Pro | Thr | Pro | Pro | Asp | Ser | Ser | Ala | Arg | Leu | Pro | Phe | Val | Thr | Leu |     |
|     |     | 20  |     |     |     |     | 25  |     |     |     |     | 30  |     |     |     |     |
| ACG | TAT | GCG | CAG | TCC | CTA | GAT | GCT | CGT | ATC | GCG | AAG | CAA | AAG | GGT | GAA | 499 |
| Thr | Tyr | Ala | Gln | Ser | Leu | Asp | Ala | Arg | Ile | Ala | Lys | Gln | Lys | Gly | Glu |     |
|     | 35  |     |     |     |     | 40  |     |     |     |     | 45  |     |     |     |     |     |
| AGG | ACG | GTT | ATT | TCG | CAT | GAG | GAG | ACC | AAG | ACA | ATG | ACG | CAT | TAT | CTA | 547 |
| Arg | Thr | Val | Ile | Ser | His | Glu | Glu | Thr | Lys | Thr | Met | Thr | His | Tyr | Leu |     |
| 50  |     |     |     |     | 55  |     |     |     |     | 60  |     |     |     |     | 65  |     |
| CGC | TAC | CAT | CAT | AGC | GGC | ATC | CTG | ATT | GGC | TCG | GGC | ACA | GCC | CTT | GCG | 595 |
| Arg | Tyr | His | His | Ser | Gly | Ile | Leu | Ile | Gly | Ser | Gly | Thr | Ala | Leu | Ala |     |
|     |     |     |     | 70  |     |     |     |     | 75  |     |     |     |     | 80  |     |     |
| GAC | GAC | CCG | GAT | CTC | AAT | TGC | CGG | TGG | ACA | CCT | GCA | GCG | GAC | GGG | GCG | 643 |
| Asp | Asp | Pro | Asp | Leu | Asn | Cys | Arg | Trp | Thr | Pro | Ala | Ala | Asp | Gly | Ala |     |
|     |     |     |     | 85  |     |     |     |     | 90  |     |     |     |     | 95  |     |     |
| GAT | TGC | ACC | GAA | CAG | TCT | TCA | CCA | CGA | CCC | ATT | ATC | TTG | GAT | GTT | CGG | 691 |
| Asp | Cys | Thr | Glu | Gln | Ser | Ser | Pro | Arg | Pro | Ile | Ile | Leu | Asp | Val | Arg |     |
|     |     | 100 |     |     |     |     | 105 |     |     |     |     | 110 |     |     |     |     |
| GGC | AGA | TGG | AGA | TAC | CGC | GGG | TCC | AAA | ATA | GAG | TAT | CTG | CAT | AAC | CTT | 739 |
| Gly | Arg | Trp | Arg | Tyr | Arg | Gly | Ser | Lys | Ile | Glu | Tyr | Leu | His | Asn | Leu |     |
|     | 115 |     |     |     |     | 120 |     |     |     |     | 125 |     |     |     |     |     |
| GGC | AAG | GGG | AAG | GCG | CCC | ATA | GTG | GTC | ACG | GGG | GGT | GAG | CCG | GAG | GTC | 787 |
| Gly | Lys | Gly | Lys | Ala | Pro | Ile | Val | Val | Thr | Gly | Gly | Glu | Pro | Glu | Val |     |
| 130 |     |     |     |     | 135 |     |     |     |     | 140 |     |     |     |     | 145 |     |
| CGC | GAA | CTA | GGC | GTC | AGT | TAC | CTG | CAG | CTG | GGT | GTC | GAC | GAG | GGT | GGC | 835 |
| Arg | Glu | Leu | Gly | Val | Ser | Tyr | Leu | Gln | Leu | Gly | Val | Asp | Glu | Gly | Gly |     |
|     |     |     |     | 150 |     |     |     |     | 155 |     |     |     |     | 160 |     |     |
| CGC | TTG | AAT | TGG | GGC | GAG | TTG | TTT | GAG | CGA | CTC | TAT | TCT | GAG | CAC | CAC | 883 |
| Arg | Leu | Asn | Trp | Gly | Glu | Leu | Phe | Glu | Arg | Leu | Tyr | Ser | Glu | His | His |     |
|     |     |     | 165 |     |     |     |     | 170 |     |     |     |     | 175 |     |     |     |
| CTG | GAA | AGT | GTC | ATG | GTC | GAA | GGC | GGC | GCG | GAG | GTG | CTC | AAC | CAG | CTG | 931 |
| Leu | Glu | Ser | Val | Met | Val | Glu | Gly | Gly | Ala | Glu | Val | Leu | Asn | Gln | Leu |     |
|     |     | 180 |     |     |     |     | 185 |     |     |     |     | 190 |     |     |     |     |
| CTG | CTG | CGC | CCA | GAT | ATT | GTG | GAC | AGT | CTG | GTG | ATC | ACG | ATA | GGA | TCC | 979 |
| Leu | Leu | Arg | Pro | Asp | Ile | Val | Asp | Ser | Leu | Val | Ile | Thr | Ile | Gly | Ser |     |
|     | 195 |     |     |     |     | 200 |     |     |     |     | 205 |     |     |     |     |     |
| AAG | TTC | CTG | GGC | TCA | CTA | GGT | GTT | GCG | GTC | TCA | CCA | GCT | GAG | GAG | GTG | 1027 |
| Lys | Phe | Leu | Gly | Ser | Leu | Gly | Val | Ala | Val | Ser | Pro | Ala | Glu | Glu | Val |     |
| 210 |     |     |     |     | 215 |     |     |     |     | 220 |     |     |     |     | 225 |     |
| AAC | CTA | GAG | CAT | GTG | AAC | TGG | TGG | CAC | GGA | ACA | AGT | GAC | AGT | GTT | TTG | 1075 |
| Asn | Leu | Glu | His | Val | Asn | Trp | Trp | His | Gly | Thr | Ser | Asp | Ser | Val | Leu |     |
|     |     |     |     | 230 |     |     |     |     | 235 |     |     |     |     | 240 |     |     |

```
TGC GGC CGG CTC GCA TAGCGGTTAT GACTGGTCTA CTAGTTAAAA CTATTTACTC        1130
Cys Gly Arg Leu Ala
        245

CTATACATAT TGCGTCACAT AGCGTTTATC CCCCTCGCCA ACCGCCTCGT GCCGTTGGAA      1190

ACACGGCGGC CGGGGGACCT CAAGCGCTCC GCATCGACTA GTTTAATTTA CAAACAGATT      1250

CTGTAACTTG CGTAACGGCC AGAGGTCTCT GACTTTCTGA TAATCTTCAC CACCTCACCT      1310

CGCTTCAACC CCAGGTATAA TGCAACTTGG ATCCATCCTC TGGATTCTAG GTAACTGAGA      1370

TTCCTTTAAC CTGTATCTCT TCAACAACTC CTTCTTTTCT TCGTCGCTGA GTTTGATATG      1430

TTTTGGCACA AGCTCATGGT GCGTGATATT TACCACCAAA GCTGTTTCGT TGAAAGTCTC      1490

AATTGTAGCA GGAGCGACGG AGGGAAGCAG TTTCAACGCG CTGGGCGTTA TGCCGTTCTG      1550

ATATATGAAA ATACCCGTCT GGAAGTTCTT CTCGCCAATG TGGATC                    1596
```

(2) INFORMATION FOR SEQ ID NO: 12:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ala Leu Ile Pro Leu Ser Gln Asp Leu Ala Asp Ile Leu Ala Pro
 1               5                  10                  15

Tyr Leu Pro Thr Pro Pro Asp Ser Ser Ala Arg Leu Pro Phe Val Thr
                20                  25                  30

Leu Thr Tyr Ala Gln Ser Leu Asp Ala Arg Ile Ala Lys Gln Lys Gly
                35                  40                  45

Glu Arg Thr Val Ile Ser His Glu Glu Thr Lys Thr Met Thr His Tyr
        50                  55                  60

Leu Arg Tyr His His Ser Gly Ile Leu Ile Gly Ser Gly Thr Ala Leu
65                      70                  75                  80

Ala Asp Asp Pro Asp Leu Asn Cys Arg Trp Thr Pro Ala Ala Asp Gly
                85                  90                  95

Ala Asp Cys Thr Glu Gln Ser Ser Pro Arg Pro Ile Ile Leu Asp Val
                100                 105                 110

Arg Gly Arg Trp Arg Tyr Arg Gly Ser Lys Ile Glu Tyr Leu His Asn
                115                 120                 125

Leu Gly Lys Gly Lys Ala Pro Ile Val Val Thr Gly Gly Glu Pro Glu
                130                 135                 140

Val Arg Glu Leu Gly Val Ser Tyr Leu Gln Leu Gly Val Asp Glu Gly
145                 150                 155                 160

Gly Arg Leu Asn Trp Gly Glu Leu Phe Glu Arg Leu Tyr Ser Glu His
                165                 170                 175

His Leu Glu Ser Val Met Val Glu Gly Gly Ala Glu Val Leu Asn Gln
                180                 185                 190

Leu Leu Leu Arg Pro Asp Ile Val Asp Ser Leu Val Ile Thr Ile Gly
                195                 200                 205

Ser Lys Phe Leu Gly Ser Leu Gly Val Ala Val Ser Pro Ala Glu Glu
        210                 215                 220

Val Asn Leu Glu His Val Asn Trp Trp His Gly Thr Ser Asp Ser Val
225                 230                 235                 240

Leu Cys Gly Arg Leu Ala
                245
```

RIBOFLAVIN-BIOSYNTHESIS IN FUNGI

This application is national stage application of PCT/EP95/00958, filed on Mar. 15, 1995.

The present invention relates to the genes for riboflavin biosynthesis in fungi, to the proteins encoded thereby and to genetic engineering processes for preparing riboflavin using these genes and gene products.

The preparation of riboflavin by fermentation of fungi such as Eremothecium ashbyii or Ashbya gossypii has been disclosed (The Merck Index, Windholz et al., eds. Merck & Co., page 1183 (1983)).

EP 405370 describes riboflavin-overproducing bacterial strains which have been obtained by transformation of the riboflavin bio- synthesis genes from Bacillus subtilis.

Since the genetics of riboflavin biosynthesis in bacteria and eu- karyotes differ, the abovementioned genes from Bacillus subtilis are unsuitable for a recombinant process for preparing riboflavin using eukaryotic producer organisms such as Ashbya gossypii.

The cloning of the riboflavin biosynthesis genes of the yeast Saccharomyces cerevisiae was described in a patent application filed at the German Patent Office on Nov. 19, 1992.

However, it was not possible to clone the Ashbya gos- sypii ribo- flavin biosynthesis genes using the S. cerevisiae rib genes by conventional hybridization methods; evidently the homology of the rib genes from S. cerevisiae and A. gossypii was not great enough for hybridization.

It is an object of the present invention to isolate the ribo- flavin biosynthesis genes from a eukaryote in order in this way to provide a recombinant process for preparing ribo- flavin in a eukaryotic producer organism.

We have found that this object is achieved by isolation of six genes (rib genes) found in the ascomycete Ashbya gossypii which code for enzymes of riboflavin biosynthesis starting from GTP.

The invention relates to the following DNA sequences:

DNA sequences which code for a polypeptide with the amino-acid sequence depicted in SEQ ID NO: 2, or for an analog or derivative of the polypeptide shown in SEQ ID NO: 2, in which one or more amino acids have been deleted, added or replaced by other amino acids, without essentially reducing the enzymatic action of the polypeptide.

DNA sequences which code for a polypeptide with the amino-acid sequence depicted in SEQ ID NO: 4, or for an analog or derivative of the polypeptide shown in SEQ ID NO: 4, in which one or more amino acids have been deleted, added or replaced by other amino acids, without essentially reducing the enzymatic action of the polypeptide.

DNA sequences which code for a polypeptide with the amino-acid sequence depicted in SEQ ID NO: 6, or for an analog or derivative of the polypeptide shown in SEQ ID NO: 6, in which one or more amino acids have been deleted, added or replaced by other amino acids, without essentially reducing the enzymatic action of the polypeptide.

DNA sequences which code for a polypeptide with the amino-acid sequence depicted in SEQ ID NO: 8, or for an analog or derivative of the polypeptide shown in SEQ ID NO: 8, in which one or more amino acids have been deleted, added or replaced by other amino acids, without essentially reducing the enzymatic action of the polypeptide.

DNA sequences which code for a polypeptide with the amino-acid sequence depicted in SEQ ID NO: 10, or for an analog or derivative of the polypeptide shown in SEQ ID NO: 10, in which one or more amino acids have been deleted, added or replaced by other amino acids, without essentially reducing the enzymatic action of the polypeptide.

DNA sequences which code for a polypeptide with the amino-acid sequence depicted in SEQ ID NO: 12, or for an analog or derivative of the polypeptide shown in SEQ ID NO: 12, in which one or more amino acids have been deleted, added or replaced by other amino acids, without essentially reducing the enzymatic action of the polypeptide.

The genes and their gene products (polypeptides) are shown in the sequence listing with their primary structure and are assigned as follows:

SEQ ID NO: 1: rib 1 gene
SEQ ID NO: 2: rib 1 gene product (GTP cyclohydrolase II)
SEQ ID NO: 3: rib 2 gene
SEQ ID NO: 4: rib 2 gene product (DRAP deaminase)
SEQ ID NO: 5: rib 3 gene
SEQ ID NO: 6: rib 3 gene product (DBP synthase)
SEQ ID NO: 7: rib 4 gene
SEQ ID NO: 8: rib 4 gene product (DMRL synthase)
SEQ ID NO: 9: rib 5 gene
SEQ ID NO: 10: rib 5 gene product (riboflavin synthase)
SEQ ID NO: 11: rib 7 gene
SEQ ID NO: 12: rib 7 gene product (HTP reductase)

Guanosine triphosphate (GTP) is converted by GTP cyclohydrolase II (rib 1 gene product) into 2,5-diamino-6-ribosylamino-4(3H)-pyrimidinone 5-phosphate. This com- pound is subsequently reduced by the rib 7 gene product to 2,5-diaminoribitylamino-2,4(1H,3H)-pyrimidine 5-phosphate and then deaminated by the rib 2 gene product to 5-amino-6-ribitylamino-2,4(1H,3H)-pyrimidinedione. Subsequently, in a reaction catalyzed by the rib 4 gene product, the C4 compound DBP is added on to result in 6,7-dimethyl-8-ribitvllumazine (DMRL), from which ribo- flavin is produced in the reaction catalyzed by the rib 5 gene product. The C4 compound DBP (L-3,4-dihydroxy-2-butanone 4-phosphate) is formed from D-ribulose 5-phosphate in a reaction catalyzed by the rib 3 gene product.

The DNA sequences described in SEQ ID NO: 1, 3, 5, 7, 9, 11 code for the polypeptides described in SEQ ID NO: 2, 4, 6, 8, 10, 12.

DNA sequences, apart from those specified in the sequence list- ing, which are also suitable are those which, as a consequence of the degeneracy of the genetic code, have a different DNA sequence but code for the same polypeptide.

The invention also relates to those DNA sequences which code for a gene product (polypeptide) with a primary structure other than that detailed in the sequence listing as long as the gene product still has essentially the same biological properties as the gene product specified in the sequence listing. Biological properties mean, in particular, the enzymatic activities bringing about the biosynthesis of riboflavin.

Such modified gene products with essentially the same biological properties can be obtained by deletion or addition of one or more amino acids or peptides or by replacing amino acids by other ami- no acids, or can be isolated from organisms other than Ashbya gossypii.

The DNA sequences which code for the modified gene products are, as a rule, homologous to the extent of 80 percent or more with the DNA sequences shown in the sequence listing. Such DNA sequences can be isolated starting from the DNA sequences described in SEQ ID NO: 1, 3, 5, 7, 9, 11, for example with conventional hybridization methods or the PCR technique from eukaryotes other than Ashbya gossypii. These DNA sequences hybridize under standard conditions with the DNA sequences described in SEQ ID NO: 1, 3, 5, 7, 9, 11.

Standard conditions mean, for example, temperatures from 42 to 58° C. in an aqueous buffer solution with a concentration of from 0.1 to 1 × SSC (1 × SSC: 0.15 M NaCl, 15 mM sodium citrate pH 7.2). The experimental conditions for DNA hybridizations are described in textbooks of genetic engineering, for example in Sambrook et al., "Molecular Cloning", Cold Spring Harbor Laboratory, 1989.

The invention also relates to regulating sequences, in particular promoter sequences, which are located upstream in the 5' direction of the DNA sequences coding for the appropriate polypeptide. The regulating sequences are specified in the sequence listing and explained in detail below.

Regulating sequence for rib 1 gene: SEQ ID NO: 1 nucleotide 1-242

Regulating sequence for rib 2 gene: SEQ ID NO: 3 nucleotide 1-450

Regulating sequence for rib 3 gene: SEQ ID NO: 5 nucleotide 1-314

Regulating sequence for rib 4 gene: SEQ ID NO: 7 nucleotide 1-270

Regulating sequence for rib 5 gene: SEQ ID NO: 9 nucleotide 1-524

Regulating sequence for rib 7 gene: SEQ ID NO: 11 nucleotide 1-352

The regulating sequences can also be truncated in the 5' and/or 3' direction with negligible diminution in their functioning.

Essential for the regulating action are, as a rule, fragments of 30–100, preferably 40–70, nucleotides from the above-mentioned sequence regions.

These regulating sequences can also be optimized in their functioning, by comparison with the natural sequences, by directed mutagenesis.

The regulating sequences according to the invention are suitable for overexpression of genes in Ashbya, in particular of genes responsible for riboflavin biosynthesis.

The invention also relates to expression vectors which contain one or more of the DNA sequences according to the invention. Such expression vectors are obtained by providing the DNA sequences according to the invention with suitable functional regulating signals. Such regulating signals are DNA sequences which are responsible for the expression, for example promoters, operators, enhancers, ribosome binding sites, and which are recognized and obeyed by the host organism.

It is also possible where appropriate for the expression vector to comprise other regulating signals which, for example, control replication or recombination of the recombinant DNA in the host organism.

The invention likewise relates to the host organisms transformed with the DNA sequences or expression vectors according to the invention. Eukaryotic organisms are preferably used as host organisms, particularly preferably those of the genus Saccharomyces, Candida, Pichia, Eremothecium or Ashbya. Particularly preferred species are Saccharomyces cerevisiae, Candida flaveri, Candida famata, Eremothecium ashbyii and Ashbya gossypii.

The invention also includes a recombinant process for preparing riboflavin in which the transformed host organisms according to the invention are cultured in a conventional way by fermentation, and the riboflavin produced during the fermentation is isolated from the fermentation medium and, where appropriate, purified.

The rib genes and gene products can be isolated and characterized as described in the example and in the sequence listing.

EXAMPLE 1

Isolation of the Ashbya gossypii riboflavin biosynthesis genes (rib genes)

a. Construction of an Ashbya gossypii cDNA bank

RNA was completely extracted from the mycelium of the riboflavin-overproducing strain Ashbya gossypii ATCC 10195 in the late logarithmic phase of growth after cultivation on YEPD medium (Sherman et al., "Methods in yeast genetics", Cold Spring Harbor, N.Y., 1989).

Poly(A)$^+$ RNA was purified by adsorption on and elution from oligo(dT)-cellulose twice (Aviv and Leder, Proc. Natl. Acad. Sci. USA 69, 1972, 1408–1412). The cDNA was isolated by the general method of Gubler and Hoffmann (Gene 25, 1983, 263), and synthetic EcoRI adaptors were added on to the ends of the blunt-ended cDNA molecules. The cDNA fragments after cutting with EcoRI were subsequently phosphorylated using T4 polynucleotide kinase and cloned into the dephosphorylated vector pYEura3 which had been cut with EcoRI (FIG. 1). pYEura3 (Clonetech Laboratories, Inc., Calif.) is a yeast expression vector which contains the galactose-inducible GALL and GALIO promoters and URA, CEN4 and ARS1. These yeast elements permit the transformation and expres- sion of cloned DNA fragments in yeast cells.

Aliquots from the ligation reaction were used to transform highly competent (Hanahan, DNA Cloning, ed. D.M. Glover; IRL Press, oxford 1985, 109) E. coli XL1-Blue (Bullock et al., Biotechniques 5 (1987) 376–378), and transformants were selected on the basis of their ampicillin resistance.

About 3×10$^5$ ampicillin-resistant cells were combined and ampli- fied, and plasmid DNA was isolated therefrom (Birnboim and Doly, Nucleic Acids Res. 7, 1979, 1513).

b. Isolation of Ashbya gossypii cDNA clones which code for riboflavin-producing enzymes cDNA clones from Ashbya gossypii which code for riboflavin- producing enzymes were isolated by functional complementation of Saccharomyces cerevisiae mutants involved in riboflavin biosynthesis.

The strains AJ88 (Mata leu2 his3 rib1::URA3 ura3–52), AJ115 (Matalpha leu2 inos1 rib2::URA3 ura3–52), AJ71 (Matalpha leu2 inos1 rib3::URA3 ura3–52), AJ106 (Matalpha leu2 inos1 rib4::URA3 ura3–52), AJ66 (Mata canR inos1 rib5::URA3 ura3–52) and AJ121 (Matalpha leu2 inos1 rib7::URA3 ura3–52) are mutated strains produced by destruction of one of the six genes (rib1 to rib5 and rib7) involved in riboflavin biosynthesis in Saccharomyces cerevisiae.

These strains were each transformed with 25 µg of cDNA from the Ashbya gossypii CDNA bank and plated on solid galactose-containing medium without riboflavin. After growth for approximately one week, rib$^+$ transformants were isolated from the culture dishes.

In each case one transformant from each transformed mutant (Rib1+, Rib2+, Rib3+, Rib4+, Rib5+ and Rib7+) was analyzed and it was found in all cases that the Rib$^+$ phenotype was expressed only in galactose medium but not in glucose medium.

These results demonstrate that the Rib+ phenotype was expressed under the control of the galactose-inducible GAL10 promoter located on the plasmid.

Plasmid DNA was isolated from the Rib1+, Rib2+, Rib3+, Rib4+, Rib5+ and Rib7+ transformants by transformation of E. coli and was called pJR715, pJR669, pJR788, pJR733, pJR681 and pJR827.

Partial sequencing of the cDNA inserts present in these plasmids confirmed that they code for proteins which are analogous to proteins of the rib gene products from Saccharomyces.

c. Isolation of Ashbya gossypii genomic clones which code for ri- boflavin-producing enzymes In order to isolate the genomic copies of the riboflavin-producing genes of Ashbya gossypii, a genomic bank of Ashbya gossypii ATCC 10195 was constructed in the cosmid supercos1 (Stratagene Cloning Systems, Calif.) and screened with $^{32}$P-labeled probes which were derived from the cDNA copies of the rib1, rib2, rib3, rib4, rib5 and rib7 genes of Ashbya gossypii.

Cosmid clones with rib1, rib2, rib3, rib4, rib5 and rib7 DNA were isolated by colony hybridization (Grunstein and Hogness, Proc. Natl. Acad. Sci. USA 72, 1975, 3961–3965). Further Southern analyses of enzymatically cleaved cosmid DNA using the same rib-specific cDNA probes made it possible to identify defined restriction fragments which contained the rib1, rib2, rib3, rib4, rib5 and rib7 genes of Ashbya gossypii.

Figure 2:
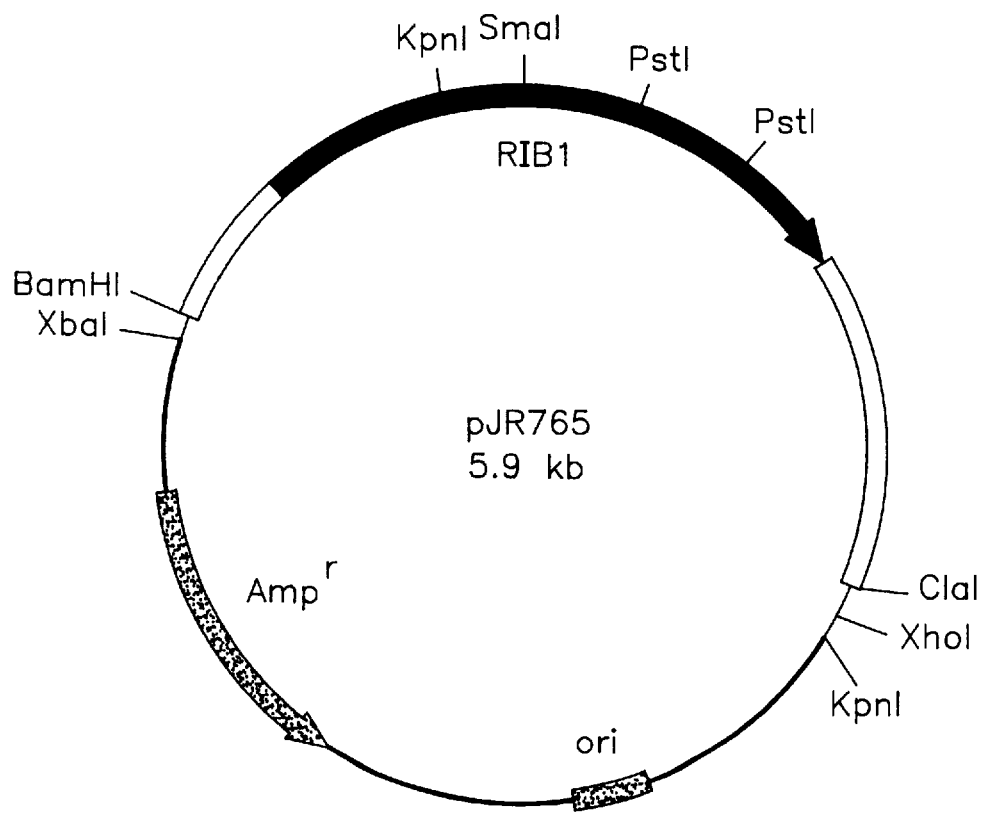

A BamHI-ClaI DNA fragment which was 3.1 kb in length and contained the complete rib1 gene of Ashbya gossypii coding for GTP cyclohydrolase II was found. This fragment was isolated from an agarose gel and cloned into the pBluescript KS (+) phagemid (Stratagene Cloning Systems) cut with BamHI and ClaI, and in this way provided the plasmid pJR765 (FIG. 2).

A DNA sequence (SEQ ID NO: 1) which was 1,329 bp in length and contained the rib1 open reading frame of 906 bp, 242 bp of the 5'-noncoding region and 181 bp of the 3'-noncoding region was ob- tained.

Figure 3:
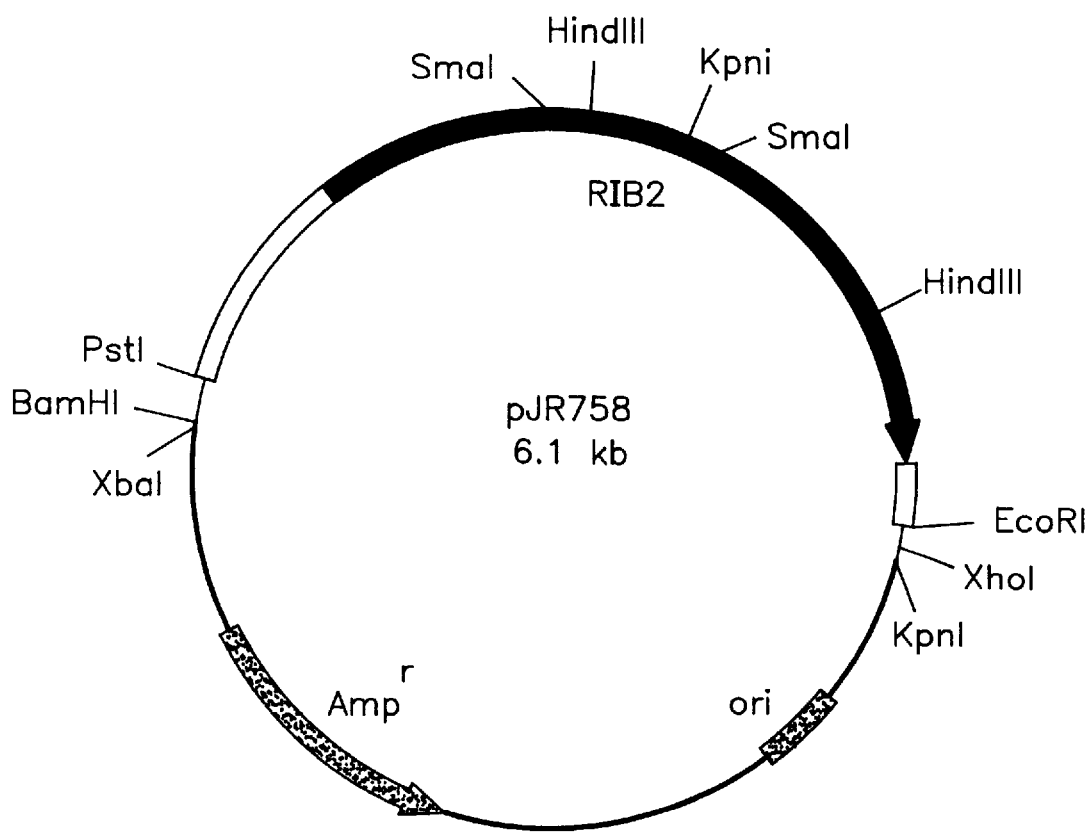

The complete Ashbya gossypii rib2 gene which codes for DRAP deaminase was found on an EcoRI-PstI fragment which was 3.0 kb in length and which, cloned into pBluescript KS (+), yielded the plasmid pJR758 (FIG. 3).

A region 2,627 bp in length from the EcoRI-PstI insert with the 1,830 bp open reading frame of rib2, 450 bp of the 5'-untranslated region and 347 bp of the 3'-untranslated region was sequenced (SEQ ID NO: 3).

Figure 4:
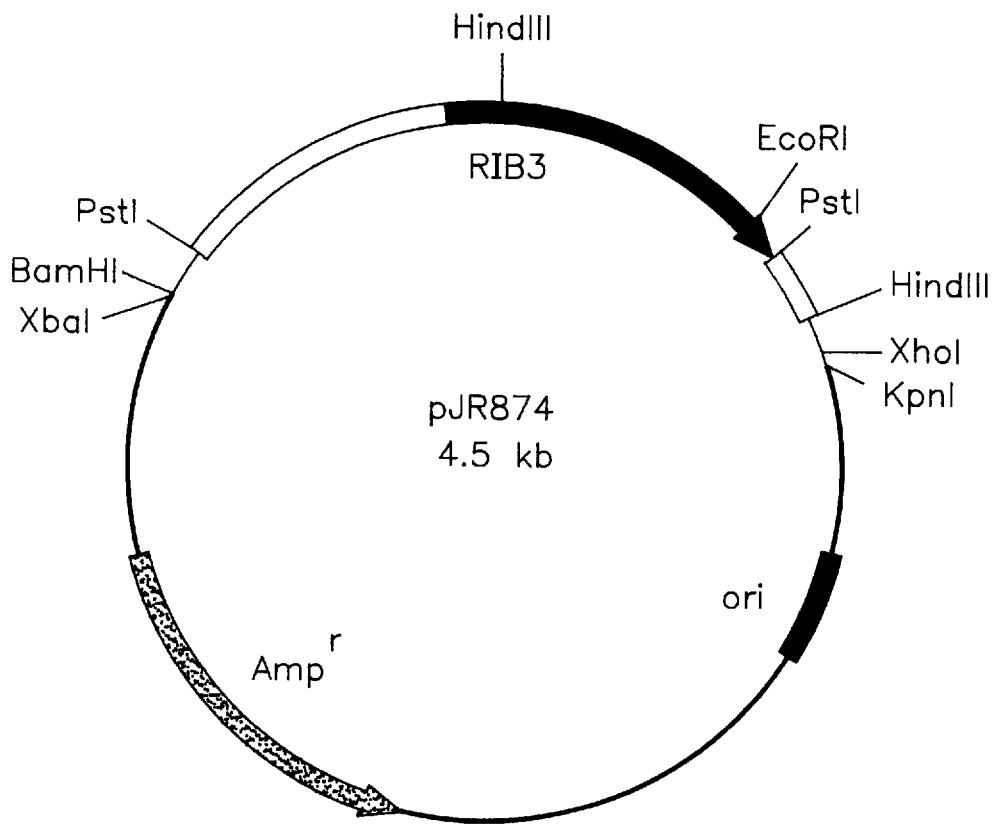

The complete Ashbya gossypii rib 3 gene which codes for DBP synthase was found on a PstI-HindIII fragment which was 1.5 kb in length and, cloned into pBluescript KS (+), yielded the plasmid pJR790 (FIG. 4).

A region 1,082 bp in length from the PstI-HindIII insert with the 639 bp open reading frame of rib 3, 314 bp of the 5'-untranslated region and 129 bp of the 3'-untranslated region was sequenced (SEQ ID NO: 5).

Figure 5:
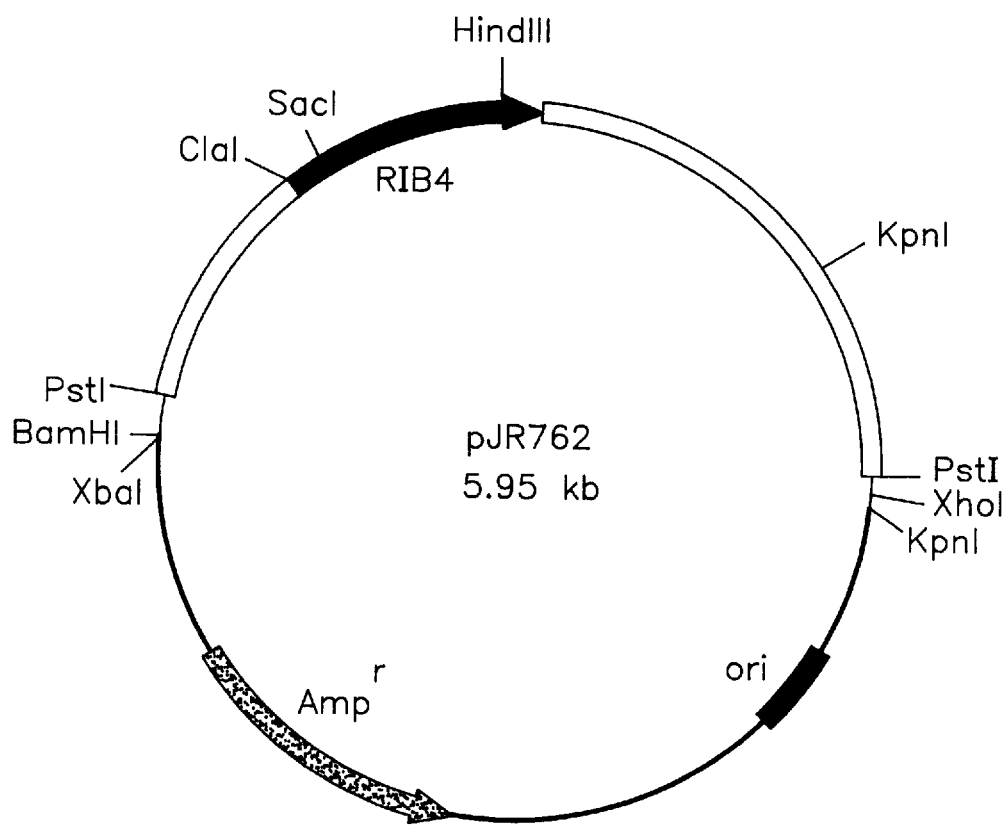

The Ashbya gossypii rib4 gene which codes for DMRL synthase was found on a PstI-PstI fragment which was 3.2 kb in length and, cloned into pBluescript KS (+), yielded the plasmid pJR762 (FIG. 5).

A region 996 bp in length from the PstI-PstI insert with the 519 bp open reading frame of rib4, 270 bp of the 5'-untranslated region and 207 bp of the 3'-untranslated region was sequenced (SEQ ID NO: 7).

Figure 6:
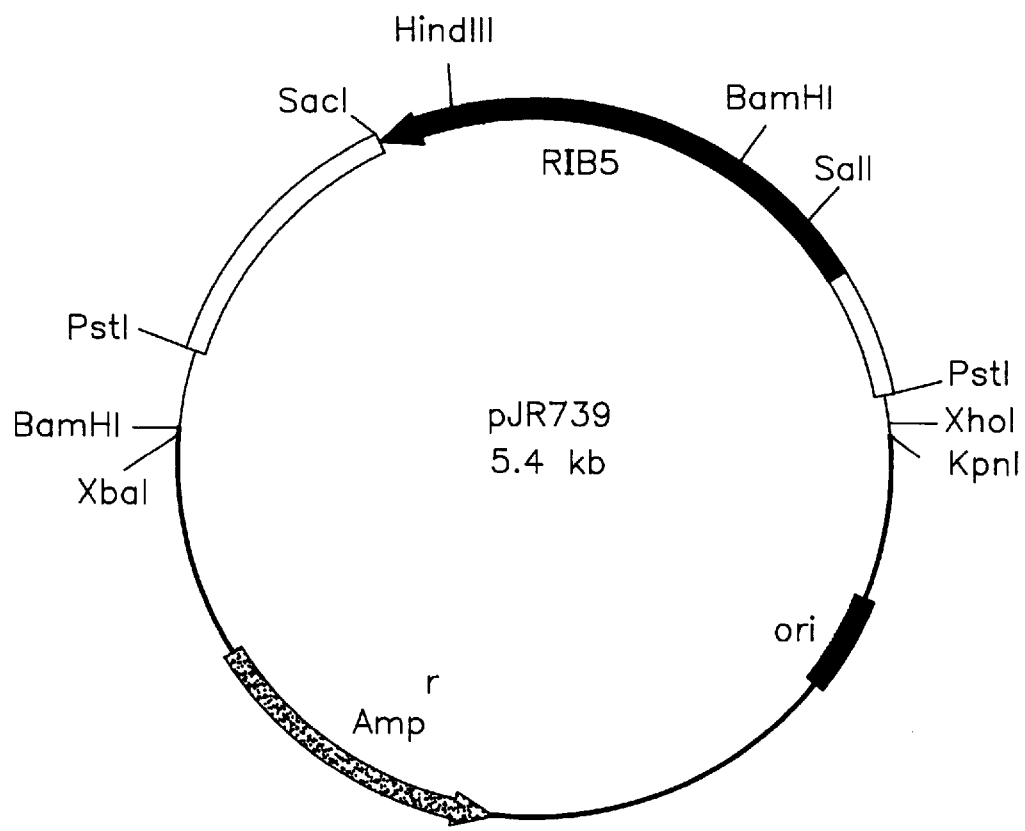

The complete Ashbya gossypii rib5 gene which codes for riboflavin synthase was found on a PstI-PstI fragment which was 2.5 kb in length and, cloned into pBluescript KS (+), yielded the plasmid pJR739 (FIG. 6).

A region 1,511 bp in length from the PstI-PstI insert with the 708 bp open reading frame of rib5, 524 bp of the 5'-untranslated region and 279 bp of the 3'-untranslated region was sequenced (SEQ ID NO: 9).

Figure 7:
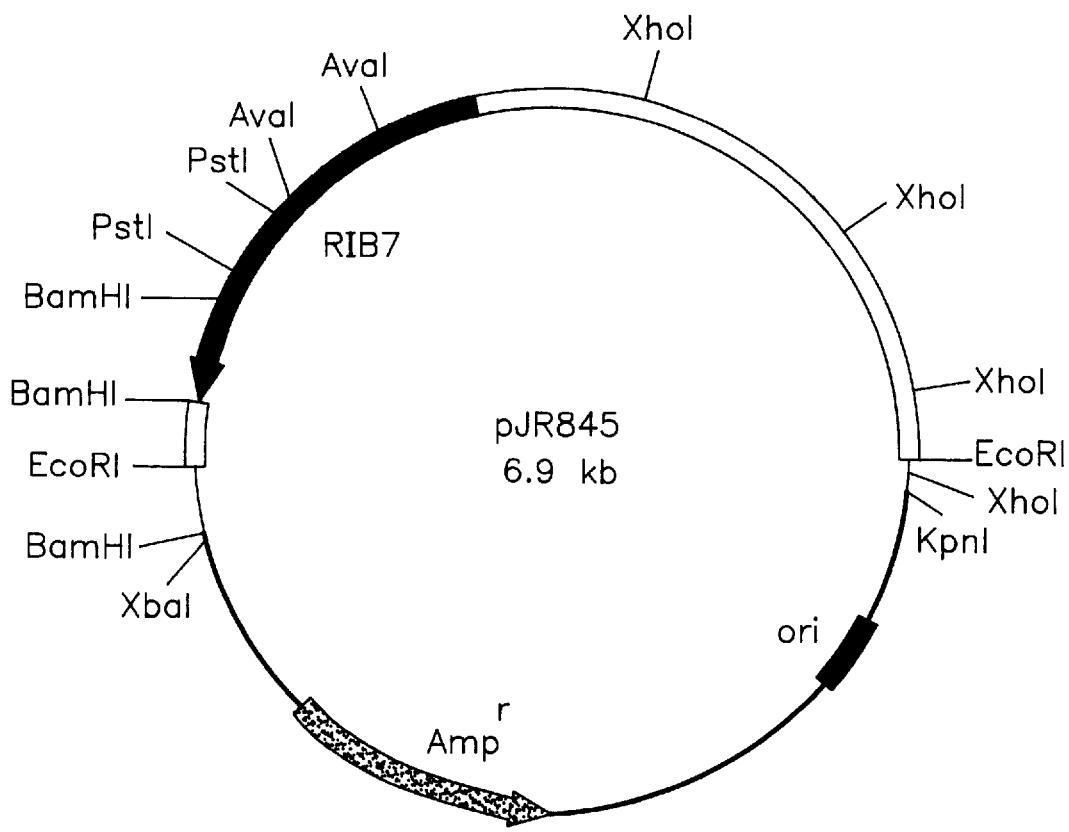

Finally, the Ashbya gossypii rib7 gene which codes for HTP reductase was found on an EcoRI-EcoRI fragment which was 4.1 kb in length and, cloned into pBluescript KS (+), yielded the plasmid pJR845 (FIG. 7).

A region 1,596 bp in length from the EcoRI-EcoRI insert with the 741 bp open reading frame of rib7, 352 bp of the 5'-untranslated region and 503 bp of the 3'-untranslated region was sequenced (SEQ ID NO: 11).

EXAMPLE 2 mRNA analysis of the Ashbya gossypii rib genes

Northern analyses were carried out to identify the rib-specific transcripts. The total RNA was isolated from the Ashbya gossypii strain ATCC 10195 as described in Example 1. The RNA samples from the strain (5 μg) were fractionated by electrophoresis on 0.8% agarose formaldehyde gels together with RNA size markers and blotted in vacuo onto nylon membranes (Thomas, Proc. Natl. Acad. Sci. USA, 77, 1980, 5201–5205).

The nylon membranes were separately hybridized with $^{32}$P-labeled rib-specific DNA probes at 42° C. in 5 × SSC and in the presence of 50% formamide. The Ashbya gossypii rib1 gene is expressed as unique message of about 1,150 nucleotides, which was detected in both strains by an SmaI-SacI probe 0.7 kbp in length from the plasmid pJR765 (FIG. 8).

In a similar way, unique 1,900 nucleotide-long rib2, 900 nucleotide-long rib3, 800 nucleotide-long rib4, 1,050 nucleotidelong rib5 and 1,000 nucleotide-long rib7 transcripts were detected in the blots using an SmaI-SmaI fragment 0.5 kbp in length from pJR758, a HindIII-KpnI fragment 0.6 kbp in length from pJR790, an ScaI-HindIII fragment 0.5 kbp in length from pJR739 and a PstI-PstI fragment 0.3 kbp in length from pJR845 as specific probe.

EXAMPLE 3

Expression of the Ashbya gossypii rib genes in Saccharomyces cerevisiae

It is possible as described in Example 1 to grow Saccharomyces cerevisiae mutants which have been well investigated and are defective in one stage of riboflavin biosynthesis on culture media without riboflavin if they harbor a plasmid which codes for the complementing Ashbya enzymes. In order to test the function of the Ashbya gossypii rib gene products, flavin-producing enzyme activities were measured in cell-free extracts from S. cerevisiae mutants which harbored one of the expression plasmids pJR715, pJR669, pJR788, pJR733, pJR681 and pJR827.

These plasmids which are derived from pYEura3 and are described in Example 1 contain Ashbya gossypii rib-specific cDNA fragments under the control of the galactose-inducible GAL10 promoter.

Cell-free protein extracts from S. cerevisiae were obtained from cultures which had grown in liquid medium to an optical density of about 2 OD.

The cells were harvested, washed with cold 20 mM tris HCl, pH 7.5, and resuspended in the same buffer, which was supplemented with 1 mM phenylethylsulfonyl fluoride.

Cell lysates were prepared by vortexing in the presence of glass beads and centrifuging at 3,000 g and 4° C. for 20 min.

GTP cyclohydrolase II, DRAP deaminase, DBP synthase, DMRL synthase, riboflavin synthase and HTP reductase enzyme activities were determined as described in the literature (Shavlovsky et al., Arch. Microbiol. 124, 1980, 255–259; Richter et al., J. Bacteriol. 175, 1993, 4045–4051; Klein and Bacher, Z. Naturforsch. 35b, 1980, 482–484; Richter et al., J. Bacteriol. 174, 1992, 4050–4056; Nielsen et al., J. Biol. Chem. 261, 1986, 3661; Plaut and Harvey, Methods Enzymol. 18B, 1971, 515–538; Hollander and Brown, Biochem. Biophys. Res. Commun. 89, 1979, 759–763; Shavlovski et al., Biochim. Biophys. Acta, 428, 1976, 611–618).

Protein was quantified by the Peterson method (Anal. Biochem. 83, 1977, 346–356). As is evident from Tab. 1, the plasmid pJR715 brings about the expression of GTP cyclohydrolase II activity in the S. cerevisiae mutant AJ88. Furthermore, this activity is present only in cells which have grown on galactose medium, which indicates that the rib1 cDNA expression of Ashbya gossypii takes place under the control of the galactose-inducible GAL10 promoter.

These results therefore demonstrate that rib1 codes for GTP cyclohydrolase II in Ashbya gossypii. It was shown in a similar way that rib2 codes for DRAP deaminase, rib3 codes for DBP synthase, rib4 codes for DMRL synthase, rib5 codes for riboflavin synthase and rib7 codes for HTP reductase in this fungus.

TABLE 1

GTP cyclohydrolase II activity of the S. cerevisiae rib1 mutant AJ88 and its transformants.

| Strain | Plasmid | GTP cyclohydrolase II U/mg protein **) | |
|---|---|---|---|
| | | Glucose | Galactose |
| X 2180-1A* | — | 0.48 | 0.34 |
| AJ 88 | — | n.d. | n.d. |
| AJ 88 | pIR715 | n.d. | 21.60 | n.d.: not detected
*) Wild-type
**) Units of GTP cyclohydrolase II activities 1U catalyzes the formation of 1 nmol of HTP per hour

TABLE 2

DRAP deaminase activity of the S. cerevisiae rib2 mutant AJ115 and its transformants.

| Strain | Plasmid | DRAP deaminase U/mg protein *) | |
|---|---|---|---|
| | | Glucose | Galactose |
| X 2180-1A | — | 0.45 | 0.38 |
| AJ 115 | — | n.d. | n.d. |
| AJ 115 | pIR669 | n.d. | 53.22 | n.d.: not detected
*) 1U catalyzes the formation of 1 nmol of ARAP per hour

TABLE 3

DBP synthase activity of the S. cerevisiae rib3 mutant AJ71 and its transformants.

| Strain | Plasmid | DBP synthase U/mg protein *) | |
|---|---|---|---|
| | | Glucose | Galactose |
| X 2180-1A | — | 0.80 | 0.75 |
| AJ 71 | — | n.d. | n.d. |
| AJ 71 | pIR788 | n.d. | 25.19 | n.d.: not detected
*) 1U catalyzes the formation of 1 nmol of DBP per hour

TABLE 4

DMRL synthase activity of the S. cerevisiae rib4 mutant AJ106 and its transformants.

| Strain | Plasmid | DMRL synthase U/mg protein *) | |
|---|---|---|---|
| | | Glucose | Galactose |
| X 2180-1A | — | 2.04 | 1.73 |
| AJ 106 | — | n.d. | n.d. |
| AJ 106 | pIR733 | n.d. | 86.54 | n.d.: not detected
*) 1U catalyzes the formation of 1 nmol of DMRL per hour

TABLE 5

Riboflavin synthase activity of the S. cerevisiae rib5 mutant AJ66 and its transformants.

| Strain | Plasmid | Riboflavin synthase U/mg protein *) | |
|---|---|---|---|
| | | Glucose | Galactose |
| X 2180-1A | — | 4.41 | 3.80 |
| AJ 66 | — | n.d. | n.d. |
| AJ 66 | pIR681 | n.d. | 164.20 | n.d.: not detected
*) 1U catalyzes the formation of 1 nmol of riboflavin per hour

TABLE 6

HTP reductase activity of the S. cerevisiae rib7 mutant AJ121 and its transformants.

| Strain | Plasmid | HTP reductase U/mg protein *) | |
|---|---|---|---|
| | | Glucose | Galactose |
| X 2180-1A | — | 1.86 | 2.54 |
| AJ 121 | — | n.d. | n.d. |
| AJ 121 | pIR827 | n.d. | 46.21 | n.d.: not detected
*) 1U catalyzes the formation of 1 nmol of DRAP per hour

We claim:

1. An isolated DNA sequence which codes for a polypeptide with the amino acid sequence (GTP cyclohydrolase II) depicted in SEQ ID NO: 2, or for an analog or derivative of the polypeptide depicted in SEQ ID NO: 2 having essentially the same enzymatic activity as the polypeptide depicted in SEQ ID NO: 2, with the proviso that the DNA sequence of the analog or derivative of the polypeptide depicted in SEQ ID NO: 2 hybridizes with the polynucleotide depicted in SEQ ID NO: 1 at 42° C. in 5×SSC in 50% formamide solution.

2. An isolated DNA sequence which codes for a polypeptide with the amino acid sequence (DRAP deaminase) depicted in SEQ ID NO: 4, or for an analog or derivative of the polypeptide depicted in SEQ ID NO: 4 having essentially the same enzymatic activity as the polypeptide depicted in SEQ ID NO: 4, with the proviso that the DNA sequence of the analog or derivative of the polypeptide depicted in SEQ ID NO: 4 hybridizes with the polynucleotide depicted in SEQ ID NO: 3 at 42° C. in 5×SSC in 50% formamide solution.

3. An isolated DNA sequence which codes for a polypeptide with the amino acid sequence (DBP synthase) depicted in SEQ ID NO: 6, or for an analog or derivative of the polypeptide depicted in SEQ ID NO: 6 having essentially the same enzymatic activity as the polypeptide depicted in SEQ ID NO: 6, with the proviso that the DNA sequence of the analog or derivative of the polypeptide depicted in SEQ ID NO: 6 hybridizes with the polynucleotide depicted in SEQ ID NO: 5 at 42° C. in 5×SSC in 50% formamide solution.

4. An isolated DNA sequence which codes for a polypeptide with the amino acid sequence (DMRL synthase) depicted in SEQ ID NO: 8, or for an analog or derivative of the polypeptide depicted in SEQ ID NO: 8 having essentially the same enzymatic activity as the polypeptide depicted in SEQ ID NO: 8, with the proviso that the DNA sequence of the analog or derivative of the polypeptide depicted in SEQ ID NO: 8 hybridizes with the polynucleotide depicted in SEQ ID NO: 7 at 42° C. in 5×SSC in 50% formamide solution.

5. An isolated DNA sequence which codes for a polypeptide with the amino acid sequence (riboflavin synthase) depicted in SEQ ID NO: 10, or for an analog or derivative of the polypeptide depicted in SEQ ID NO: 10 having essentially the same enzymatic activity as the polypeptide depicted in SEQ ID NO: 10, with the proviso that the DNA sequence of the analog or derivative of the polypeptide depicted in SEQ ID NO:10 hybridizes with the polynucleotide depicted in SEQ ID NO: 9 at 42° C. in 5×SSC in 50% formamide solution.

6. An isolated DNA sequence which codes for a polypeptide with the amino acid sequence (HTP reductase) depicted in SEO ID NO: 12, or for an analog or derivative of the polypeptide depicted in SEQ ID NO: 12 having essentially the same enzymatic activity as the polypeptide depicted in SEQ ID NO: 12, with the proviso that the DNA sequence of the analog or derivative of the polypeptide depicted in SEQ ID NO: 12 hybridizes with the polynucleotide depicted in SEQ ID NO: 11 at 42° C. in 5×SSC in 50% formamide solution.

7. An expression vector containing one or more DNA sequences as defined in any one of the preceeding claims.

8. A host organism which has been transformed with an expression vector as defined in claim 7.

9. A recombinant method of producing riboflavin, comprising the steps of
1) constructing the expression vector defined in claim 7;
2) transforming a compatible host with said recombinant vector such that the DNA sequence coding for the polypeptide can be expressed by the host;
3) culturing the transformed host in a suitable growth medium to produce said riboflavin; and
4) recovering said riboflavin from the growth medium.

* * * * *